(12) United States Patent
Gronseth et al.

(10) Patent No.: US 9,357,979 B2
(45) Date of Patent: *Jun. 7, 2016

(54) METHOD AND SYSTEM FOR ORGANIC SPECIMEN FEATURE IDENTIFICATION IN ULTRASOUND IMAGE

(71) Applicants: Cliff A. Gronseth, Boulder, CO (US); John E. Tobey, Louisville, CO (US)

(72) Inventors: Cliff A. Gronseth, Boulder, CO (US); John E. Tobey, Louisville, CO (US)

(73) Assignee: CADUS IP LLC, Boulder, CO (US)

( * ) Notice: Subject to any disclaimer, the term of this patent is extended or adjusted under 35 U.S.C. 154(b) by 29 days.

This patent is subject to a terminal disclaimer.

(21) Appl. No.: 14/322,640

(22) Filed: Jul. 2, 2014

(65) Prior Publication Data

US 2014/0316724 A1    Oct. 23, 2014

Related U.S. Application Data

(63) Continuation of application No. 13/270,120, filed on Oct. 10, 2011, now Pat. No. 8,195,410, and a continuation-in-part of application No. 13/135,350, filed on Jul. 1, 2011, now Pat. No. 8,805,627.

(51) Int. Cl.
*G06F 19/00* (2011.01)
*A61B 8/00* (2006.01)
(Continued)

(52) U.S. Cl.
CPC ............... *A61B 8/4263* (2013.01); *A61B 8/13* (2013.01); *A61B 8/4209* (2013.01); *A61B 8/4218* (2013.01); *A61B 8/4245* (2013.01); *A61B 8/463* (2013.01); *A61B 8/5223* (2013.01); *A61B 8/5238* (2013.01); *A61B 8/464* (2013.01); *A61B 8/466* (2013.01); *A61B 8/483* (2013.01); *Y10S 128/903* (2013.01); *Y10S 128/904* (2013.01)

(58) Field of Classification Search
CPC . A61N 1/368; A61N 1/3684; A61N 1/37264; A61N 7/00; A61N 2007/00; A61B 8/00; A61B 8/4245; A61B 8/464; A61B 8/5223; A61B 8/06; G06B 8/46
USPC ......... 702/19, 20; 128/898, 903, 904; 604/26; 600/437, 443, 407; 382/128, 132; 703/2, 9

See application file for complete search history.

(56) References Cited

U.S. PATENT DOCUMENTS

| | | | | |
|---|---|---|---|---|
| 5,520,187 A | * | 5/1996 | Snyder | 600/459 |
| 5,553,618 A | * | 9/1996 | Suzuki et al. | 600/411 |
| 5,590,658 A | * | 1/1997 | Chiang et al. | 600/447 |

(Continued)

*Primary Examiner* — Carol S Tsai
(74) *Attorney, Agent, or Firm* — Tobey & Associated, LLC; Morley C. Tobey, Jr.

(57) ABSTRACT

A system, method, and non-transitory computer-readable medium. The method includes transmitting one or more reference ultrasound incident waves into an organic specimen and receiving thereby reference ultrasound data from resultant ultrasound reflected waves from specimen features in the organic specimen, identifying a reference propagation region in the organic specimen in which at least one of the one or more reference ultrasound incident waves was transmitted into the organic specimen and identifying a corresponding reference model image region in anatomic model data, and transmitting at least one additional ultrasound incident wave into the organic specimen and receiving thereby additional ultrasound data from resultant ultrasound reflected waves from one or more specimen features. Positional awareness of each ultrasound reflected wave relative to the organic specimen is maintained, and positional awareness is maintained between the reference propagation region and a propagation region of the additional ultrasound data.

37 Claims, 13 Drawing Sheets

(51) Int. Cl.
*A61B 8/08* (2006.01)
*A61B 8/13* (2006.01)

(56) References Cited

U.S. PATENT DOCUMENTS

| | | | |
|---|---|---|---|
| 5,603,323 A * | 2/1997 | Pflugrath et al. | 600/437 |
| 5,715,823 A * | 2/1998 | Wood et al. | 600/437 |
| 5,722,411 A * | 3/1998 | Suzuki et al. | 600/439 |
| 5,851,586 A * | 12/1998 | LaRose et al. | 427/208.4 |
| 5,891,035 A * | 4/1999 | Wood et al. | 600/437 |
| 5,893,363 A * | 4/1999 | Little et al. | 600/447 |
| 5,964,709 A * | 10/1999 | Chiang et al. | 600/447 |
| 6,027,451 A * | 2/2000 | McGee et al. | 600/463 |
| 6,120,449 A * | 9/2000 | Snyder et al. | 600/447 |
| 6,126,601 A * | 10/2000 | Gilling | 600/440 |
| 6,126,608 A * | 10/2000 | Kemme et al. | 600/459 |
| 6,241,673 B1 * | 6/2001 | Williams | 600/437 |
| 6,468,213 B1 * | 10/2002 | Knell et al. | 600/437 |
| 6,488,625 B1 * | 12/2002 | Randall et al. | 600/437 |
| 6,508,763 B1 * | 1/2003 | Urbano et al. | 600/437 |
| 6,524,244 B1 * | 2/2003 | Knell et al. | 600/437 |
| 6,547,730 B1 * | 4/2003 | Lin et al. | 600/437 |
| 6,659,955 B1 * | 12/2003 | Marian, Jr. | 600/459 |
| 6,669,639 B1 * | 12/2003 | Miller et al. | 600/443 |
| 6,716,172 B1 * | 4/2004 | Kerby et al. | 600/443 |
| 6,837,853 B2 * | 1/2005 | Marian | 600/437 |
| 7,092,749 B2 * | 8/2006 | Fowkes et al. | 600/407 |
| 7,591,786 B2 * | 9/2009 | Holmberg et al. | 600/437 |
| 7,604,596 B2 * | 10/2009 | Hwang et al. | 600/443 |
| 7,678,048 B1 * | 3/2010 | Urbano et al. | 600/437 |
| 7,697,973 B2 * | 4/2010 | Strommer et al. | 600/424 |
| 7,740,586 B2 * | 6/2010 | Hwang et al. | 600/443 |
| 7,840,040 B2 * | 11/2010 | Wilcox et al. | 382/128 |
| 7,850,626 B2 * | 12/2010 | Vaezy et al. | 601/2 |
| 7,867,163 B2 * | 1/2011 | Chin et al. | 600/205 |
| 7,916,322 B2 * | 3/2011 | Pineau | 358/1.15 |
| 7,918,793 B2 * | 4/2011 | Altmann et al. | 600/437 |
| 8,090,168 B2 * | 1/2012 | Washburn et al. | 382/128 |
| 2008/0275339 A1 * | 11/2008 | Thiemann et al. | 600/437 |
| 2009/0036775 A1 * | 2/2009 | Ikuma et al. | 600/443 |
| 2011/0201935 A1 * | 8/2011 | Collet-Billon et al. | 600/443 |
| 2012/0089027 A1 * | 4/2012 | Andreuccetti et al. | 600/443 |

* cited by examiner

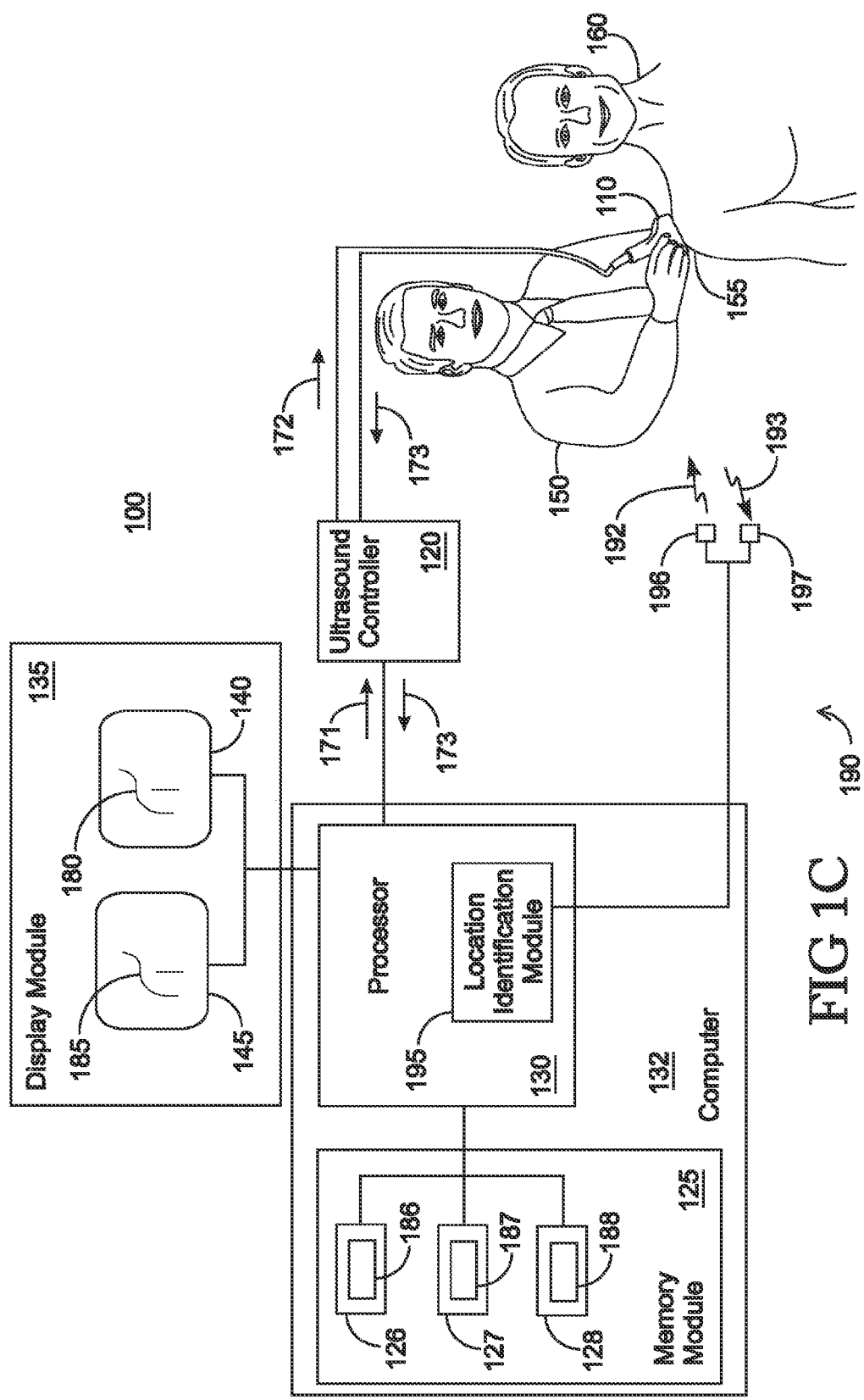

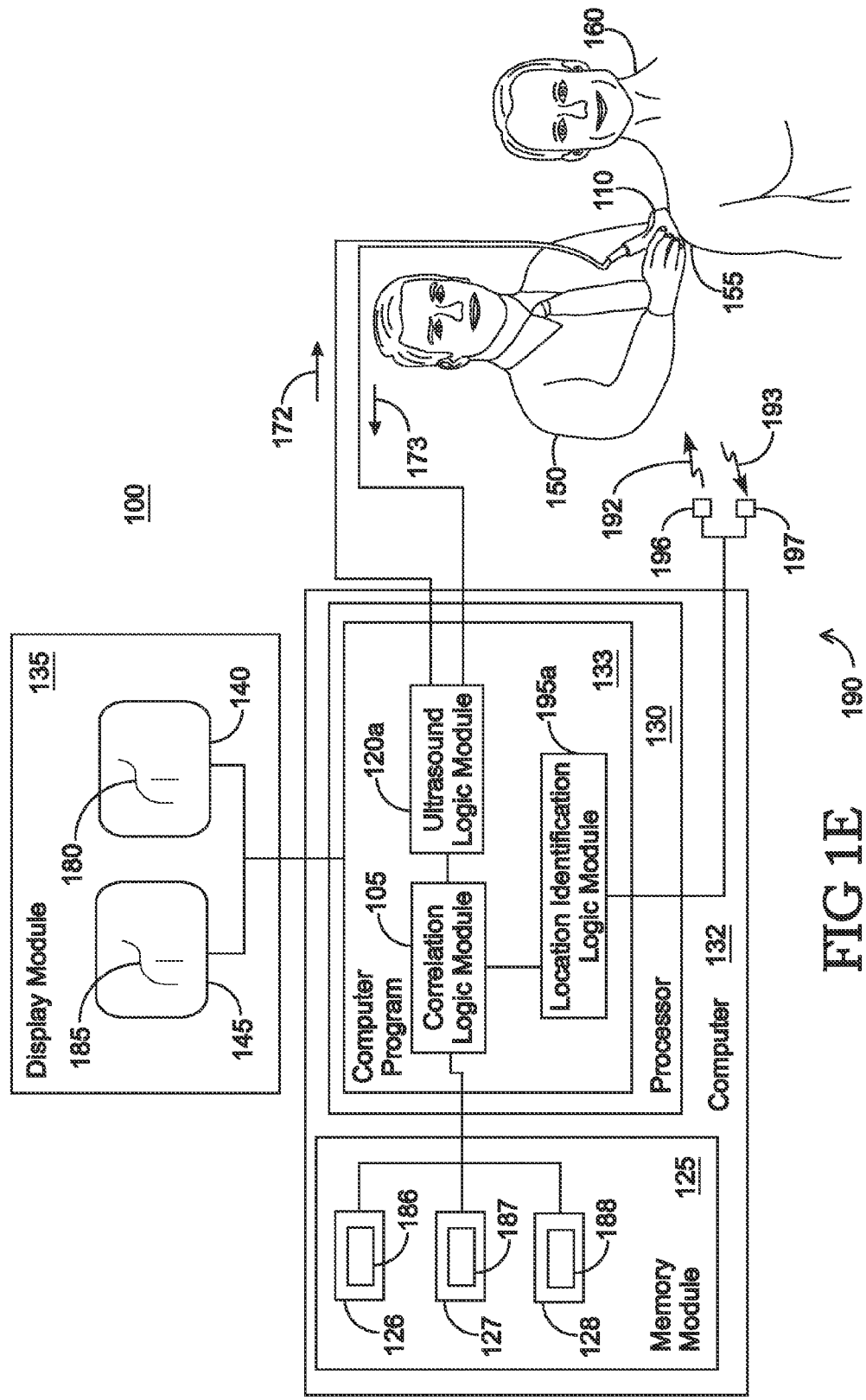

METHOD AND SYSTEM FOR ORGANIC SPECIMEN FEATURE IDENTIFICATION IN ULTRASOUND IMAGE

CROSS-REFERENCE TO RELATED APPLICATION

This application claims the priority of U.S. patent application Ser. No. 13/135,350, now issued as U.S. Pat. No. 8,805,627, by Cliff A. Gronseth and John E. Tobey, filed 1 Jul. 2011, and entitled "METHOD AND SYSTEM FOR ORGANIC SPECIMEN FEATURE IDENTIFICATION IN ULTRASOUND IMAGE" of which the entire contents are incorporated herein by reference and claims the priority of U.S. patent application Ser. No. 13/270,120, now issued as U.S. Pat. No. 8,195,410, by Cliff A. Gronseth and John E. Tobey, filed 10 Oct. 2011, and entitled "METHOD AND SYSTEM FOR ORGANIC SPECIMEN FEATURE IDENTIFICATION IN ULTRASOUND IMAGE" of which the entire contents are incorporated herein by reference.

BACKGROUND

Ultrasonic waves are used in various cleaning applications, in medical diagnostic and therapeutic applications, and for a number of research and investigative purposes. Ultrasound has become a widely used, medical diagnostic tool and is generally considered to be safe as well as non-invasive. One of the more well known medical applications is in the creation of visual images of fetuses in the human womb for diagnostic purposes. In other medical areas, however, ultrasound is now used as a diagnostic tool in the creation of visual images of muscles, tendons, and various internal organs. In such applications, the size, structure, and pathological lesions of bodily soft tissues can be captured via real time tomographic images.

Compared with other diagnostic technologies, such as magnetic resonance imaging (MRI) and computed tomography (CT), ultrasound machines are relatively inexpensive and portable. While X-rays are useful for medical purposes in obtaining images of bones, ultrasonic waves find their medical applications in the creation of soft tissue images. An advantage of ultrasonic waves is that they do not have the negative biological effects associated with X-rays or with other techniques involving radioactive materials.

SUMMARY

In a first representative embodiment, a system is disclosed. The system comprises an ultrasound transducer configured for transmitting ultrasound incident waves into selected regions of an organic specimen, detecting resultant ultrasound reflected waves from specimen features of the organic specimen, and transferring ultrasound data in the resultant ultrasound reflected waves for each of multiple selected ultrasound incident waves to a processor; a location detection unit configured for detecting locations of the ultrasound transducer and the organic specimen and for transferring that location data to the processor; a memory module configured for storing anatomic model data for at least part of the organic specimen; the processor configured for identifying the region associated with selected ultrasound data using location data and one or more sets of ultrasound data resultant from reflections of recognized specimen features, creating an ultrasound image from the selected ultrasound data, obtaining model extracted data from the anatomic model data corresponding to that of the selected ultrasound data region, creating a model image from that model extracted data, and transferring the ultrasound image and the model image to a display module; and the display module configured for displaying the ultrasound image and the model image.

In a second representative embodiment, a method is disclosed. The method comprises specifying a reference model image region in model extracted data obtained from anatomic model data of at least part of an organic specimen; transmitting ultrasound incident waves into the organic specimen and receiving thereby ultrasound data from ultrasound reflected waves from specimen features in the organic specimen, wherein positional awareness of each ultrasound reflected wave relative to the organic specimen is maintained; identifying a reference propagation region corresponding to the reference model image region from paired recognized specimen features in the ultrasound data and in the model extracted data; transmitting at least one subsequent ultrasound incident wave into the organic specimen and receiving thereby subsequent ultrasound data from ultrasound reflected waves from one or more specimen features, wherein positional awareness is maintained between the reference propagation region and the propagation region of the subsequent ultrasound data; and for the subsequent ultrasound data, creating an ultrasound image, creating a model image for a model image region from the anatomic model data corresponding to the propagation region of the subsequent ultrasound data, and displaying the ultrasound image and the model image on a display module.

In an optional aspect of the second representative embodiment, the method further comprises identifying at least one specimen feature on the ultrasound image from a corresponding model feature on the model image.

In a third representative embodiment, a means for identification of an organic specimen feature in an ultrasound image is disclosed. The means comprises an ultrasound means for transmitting ultrasound incident waves into selected regions of an organic specimen, detecting resultant ultrasound reflected waves from specimen features of the organic specimen, and transferring ultrasound data in the resultant ultrasound reflected waves for each of multiple selected ultrasound incident waves to a processor means; a location detection means for detecting locations of the ultrasound means and the organic specimen and for transferring that location data to the processor means; a memory means for storing anatomic model data for at least part of the organic specimen; the processor means for identifying a region of the organic specimen associated with selected ultrasound data using location data and one or more sets of ultrasound data resultant from reflections of recognized specimen features, creating an ultrasound image from the selected ultrasound data, obtaining model extracted data from the anatomic model data corresponding to that of the selected ultrasound data region, creating a model image from the model extracted data, and transferring the ultrasound image and the model image to a display means; and the display means configured for displaying the ultrasound image and the model image.

In a fourth representative embodiment, a computer program product stored on a non-transitory computer readable storage medium for carrying out a method when executed on a computer is disclosed. The method comprises specifying a reference model image region in model extracted data obtained from anatomic model data of at least part of an organic specimen; instructing an ultrasound transducer to transmit ultrasound incident waves into the organic specimen and receiving thereby ultrasound data from ultrasound reflected waves from specimen features in the organic specimen, wherein positional awareness of each ultrasound reflected wave relative to the organic specimen is maintained; identifying a reference propagation region corresponding to the reference model image region from paired recognized specimen features in the ultrasound data and in the model extracted data; instructing an ultrasound transducer to transmit at least one subsequent ultrasound incident wave into the organic specimen and receiving thereby subsequent ultrasound data from ultrasound reflected waves from one or more specimen features, wherein positional awareness is maintained between the reference propagation region and the propagation region of the subsequent ultrasound data; and for the subsequent ultrasound data, creating an ultrasound image, creating a model image for a model image region from the anatomic model data corresponding to the propagation region of the subsequent ultrasound data, and instructing a display module to display the ultrasound image and the model image.

In a fifth representative embodiment, a non-transitory computer-readable medium having computer-executable instructions for causing a computer comprising a processor and associated memory to carry out a method is disclosed. The method comprises specifying a reference model image region in model extracted data obtained from anatomic model data of at least part of an organic specimen; instructing an ultrasound transducer to transmit ultrasound incident waves into the organic specimen and receiving thereby ultrasound data from ultrasound reflected waves from specimen features in the organic specimen, wherein positional awareness of each ultrasound reflected wave relative to the organic specimen is maintained; identifying a reference propagation region corresponding to the reference model image region from paired recognized specimen features in the ultrasound data and in the model extracted data; instructing an ultrasound transducer to transmit at least one subsequent ultrasound incident wave into the organic specimen and receiving thereby subsequent ultrasound data from ultrasound reflected waves from one or more specimen features, wherein positional awareness is maintained between the reference propagation region and the propagation region of the subsequent ultrasound data; and for the subsequent ultrasound data, creating an ultrasound image, creating a model image for a model image region from the anatomic model data corresponding to the propagation region of the subsequent ultrasound data, and instructing a display module to display the ultrasound image and the model image.

BRIEF DESCRIPTION OF THE DRAWINGS

The accompanying drawings provide visual representations which will be used to more fully describe various representative embodiments disclosed herein. They can be used by those skilled in the art to better understand the representative embodiments. In these drawings, like reference numerals identify corresponding elements.

FIG. 1C is a block diagram of still another system for identification of organic specimen features in ultrasound images as described in various representative embodiments.

FIG. 1E is a block diagram of yet still another system for identification of organic specimen features in ultrasound images as described in various representative embodiments.

DETAILED DESCRIPTION

Figure 1A:
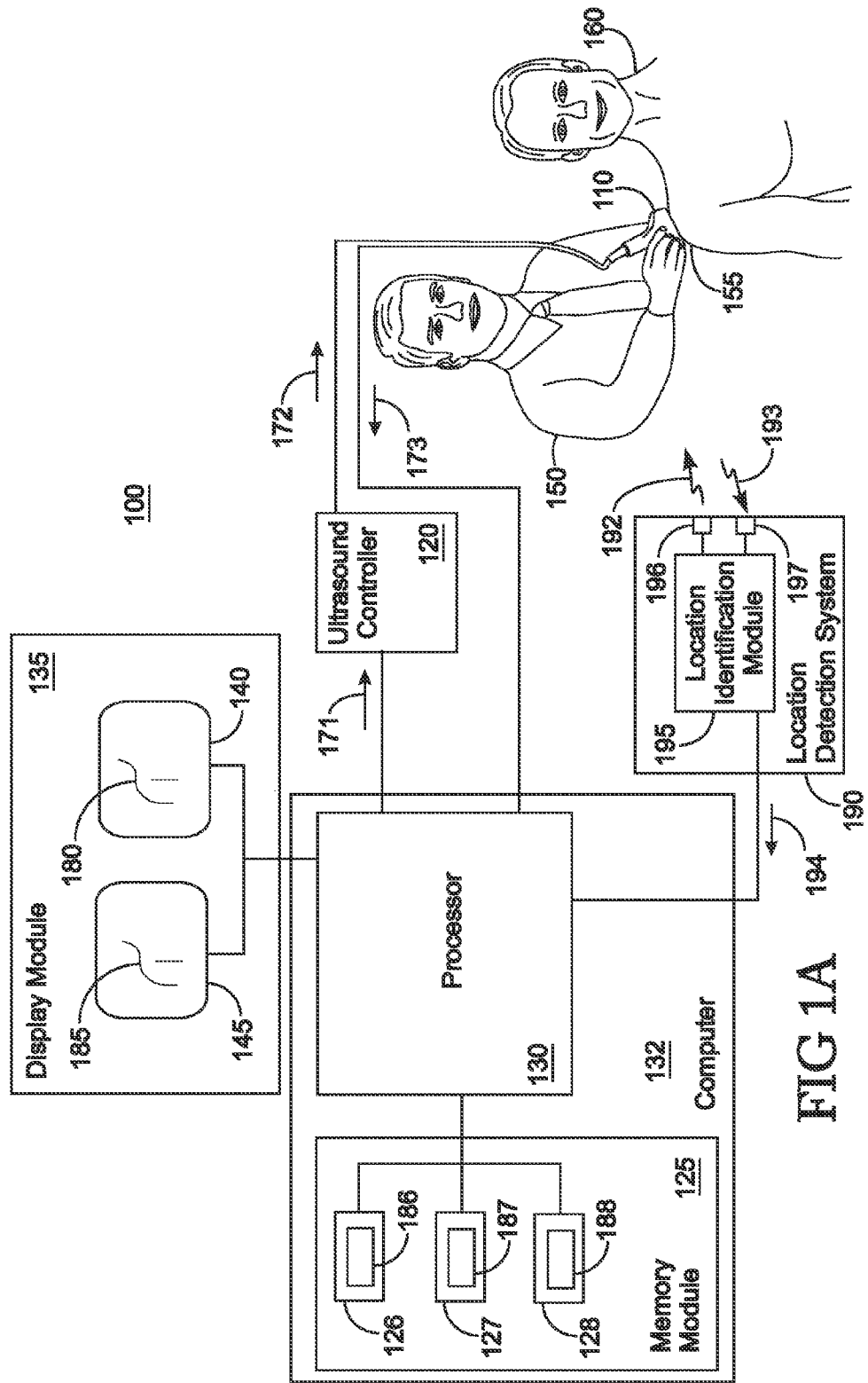
FIG. 1A is a block diagram of a system for identification of organic specimen features in ultrasound images as described in various representative embodiments.

Novel techniques are disclosed herein of methods and systems for the identification of organic features in ultrasound images of organic specimens as shown in the drawings for purposes of illustration. An organic specimen is any living or deceased organism or a portion of a living or deceased organism. In particular, the organic specimen could be a human, another animal, a plant, or a portion of a human, another animal, or a plant. The human could be a baby, an infant, a child, an adolescent, a teenager, or an adult.

Ultrasound has been used to monitor fetus development in the womb and more recently for diagnosis in musculoskeletal applications. Musculoskeletal applications include the diagnosis of muscle tears, tendon tears such as rotator cuff tears, nerve problems, blood clots in the vascular system, and the like. Musculoskeletal ultrasound images differ from those obtained in monitoring fetus development in the womb in that the musculoskeletal ultrasound transducer transmits its signal in a straight line rather than a curve. As such, a straight tendon will be displayed as a straight line on the ultrasound monitor. Such ultrasound machines are being used more and more in outpatient settings. MRI, as well as ultrasound, can be used to create images of soft, internal body tissues, but MRIs are expensive. Nuclear methods can also be used but are less desirable than ultrasound as they expose the body to radiation. Another advantage of ultrasound is that it can be used to create dynamic pictures rather than the static pictures of MRI. Ultrasound diagnostic systems provide immediate images, are portable, are safe, and are economical.

However, current systems require extensive training to develop the skills necessary for interpreting ultrasound images. Even after extensive training, inaccurate diagnoses are not uncommon, and results are often inconsistent from one operator to another. Correctly identifying a patient's internal features in an ultrasound image has been strongly dependent upon the skill of the operator that is interpreting the image. The greatest barrier to the use of ultrasound is that it must be practiced over and over again which is time consuming and expensive. The operator must be able to correctly identify the tissue displayed in an ultrasound image which means that he/she must also know anatomy in great detail as there are a large number of different parts of the human anatomy that can be detected by ultrasound. The number of operators that have had an acceptable level of this skill has been very limited, and the cost of obtaining this skill has been expensive.

Conversely, the representative embodiments disclosed herein provide systems and methods that can significantly reduce operator training time and thereby training expense, can reduce the incidence of an inaccurate diagnosis by the correct identification of tissues, and can reduce the variation from operator to operator in a diagnosis.

While the present invention is susceptible to embodiment in many different forms, there is shown in the drawings and will herein be described in detail one or more specific embodiments, with the understanding that the present disclosure is to be considered as exemplary of the principles of the invention and is not intended to limit the invention to the specific embodiments shown and described. In the following description and in the several figures of the drawings, like reference numerals are used to describe the same, similar, or corresponding parts in the several views of the drawings.

In representative embodiments, an ultrasound image obtained from an organic specimen under study is correlated with data that represents or models all or part of that organic specimen. By first identifying certain features and anatomic patterns in the organic specimen that are relatively easy to identify and correlating that information with data from the model of the organic specimen, a reference position of an ultrasound transducer with respect to the organic specimen can be identified. Then while maintaining knowledge of any subsequent movement of the ultrasound transducer and/or any subsequent movement of the organic specimen relative to the reference locations of the ultrasound transducer and the organic specimen, subsequent ultrasound images of the organic specimen can be correlated with images created from the model. This correlation enables an operator to relatively easily identify features in the organic specimen on the ultrasound image. A software program could be used to automatically identify such features. To facilitate identification of features of the organic specimen, the ultrasound and model images can be displayed simultaneously either on two separate displays or together on a single display. In alternative embodiments, the two images could be overlaid, and certain features in one or the other images could be differentially colored, displayed with dashes, dots, or otherwise differentiated lines and areas, labeled and/or otherwise appropriately identified. Also, one or the other images could be faded in and out. A computer program could provide texted or auditory identification of a specific tissue upon request. In addition, the operator could preselect particular features of interest to be emphasized when found in an ultrasound image. Such emphasis can also be added by, for example, the addition of a preselected color to the feature of interest, a flashing indicator, displayed with dashes, dots, or otherwise differentiated lines and areas, labels and/or other appropriate means. Movement of the ultrasound transducer could be programmatically controlled so as to locate preselected features on the organic specimen with little or no operator assistance.

As the ultrasound transducer is moved, the location of the ultrasound transducer relative to its identified, reference location can be maintained by a mechanical fixture attached to the ultrasound transducer, by the detection of targets placed on the ultrasound transducer using mechanical, infrared, optical, radio frequency, inertial means, or by any other acceptable means. The location of the organic specimen relative to the identified, reference location of the ultrasound transducer can be maintained by holding the organic specimen immobilized, by a mechanical fixture attached to a non-moving surface and to the organic specimen, or by the detection of targets placed on the organic specimen using, mechanical coupling, infrared, optical, radio frequency, inertial means, or by any other acceptable means.

The Visible Human Project® (VHP) is an effort to create a detailed data set from cross-sectional photographs of the human body. The Visible Human Project® is a registered trademark of the National Library of Medicine. To obtain the data, successive layers of a male and a female cadaver were removed by grinding away the top surface at regular intervals. Each of the revealed planar surfaces was photographed and stored electronically. Image data for each pixel in the two-dimensional photographs are stored in digital format along with their associated three-dimensional coordinates. Pixel image and associated coordinate data can be used to create two-dimensional and three-dimensional images of a representative human body (male or female) at diverse selected depths and angular orientations.

In representative embodiments, anatomic model data which could be, for example, the VHP data are used in combination with ultrasound data and a three-dimensional location detection device to create correlated model and ultrasound images in a human patient as well as other organic entities. These correlated images can be used to facilitate the identification of specific features in the ultrasound images of the human patient or other organic specimen. A location detection unit could use a set of targets coupled to the organic specimen and another set of targets coupled to the ultrasound transducer to acquire the location and orientation of the ultrasound transducer relative to the organic specimen. These targets could be identified and located by mechanical coupling means, optical, infrared, radio frequency, inertial means, or other appropriate techniques or by a combination of such techniques. Once the reference location of the ultrasound transducer relative to the patient (the organic specimen) is set, the location detection unit monitors any subsequent motion of the ultrasound transducer and/or the patient, identifies the related subsequent location of the ultrasound transducer and patient, and identifies, thereby, the location and orientation of the ultrasound image and the associated model image. A split screen, dual screen, or other appropriate display module can be used to view the ultrasound and model images obtained. By correlating the ultrasound and model images and by identifying features on the model image by some means which could be, for example, by the use of tags, features on the ultrasound image can be readily identified by an operator. Using such embodiments, it is no longer necessary for the operator to receive the extensive training that has previously been required. Previously several years of expensive training typically have been needed for an operator to attain the needed skill level.

Due to the large amount of data that can be associated with any given model, it may be advantageous to divide the model into different specific areas of interest such as, for example, a shoulder, an elbow, a wrist, a hip, or other specific body part. Once the operator identifies a known feature of the patient, which could be, for example, the small notch in the bones of a shoulder in which the bicep tendon passes through or other readily identifiable feature, the operator could push a button or click a mouse button to select that feature as one used for setting a plane of reference. Once the reference frame is selected, the operator could select a feature on the ultrasound image by a mouse click or other means and a program could then identify that feature and notify the operator of its identity. In representative embodiments, systems and methods disclosed herein could be used as a diagnostic tool and/or as a teaching tool.

Pathology in the anatomic model data could be digitally repaired so that the model is in pristine condition prior to its use with ultrasound images. The human anatomic model data might have, for example, a rotator cuff tear or other damage. Repairing this tear in the anatomic model data would facilitate detecting similar damage in the patient. Based on the distances between features in the ultrasound image used to set the reference location of the ultrasound transducer relative to the patient (the organic specimen), the model image can be appropriately scaled to match the size of the patient. Alternatively, the anatomic model data could have previously been scaled to certain preset representative patient sizes such as, for example, small, medium, and large and adjusted to known anatomic variants.

While the representative embodiments disclosed herein are discussed in terms of static two-dimensional model and ultrasound images, the representative embodiments can also be implemented using time varying two-dimensional model and ultrasound images, static three-dimensional model and ultrasound images, and time varying three-dimensional model and ultrasound images. As appropriate, these images can be displayed on a two-dimensional display system as static or time varying two-dimensional images and on a three-dimensional display system as static or time varying three-dimensional images.

FIG. 1A is a block diagram of a system 100 for identification of organic specimen 160 features in ultrasound images 180 as described in various representative embodiments. The system 100 comprises an ultrasound transducer 110, an ultrasound controller 120, a display module 135, a location detection unit 190, and a computer 132. The computer 132 comprises a memory module 125 and a processor 130. In FIG. 1A, the display module 135 comprises an ultrasound display 140 also referred to herein as a first display 140 and a model display 145 also referred to herein as a second display 145. The memory module 125 comprises an anatomic model memory 126, an ultrasound memory 127, and an extracted model memory 128. The location detection unit 190 comprises an emitter device 196, a receptor device 197, and a location identification module 195.

The ultrasound transducer 110 is separately coupled to the ultrasound controller 120 and to the processor 130. The processor 130 is also coupled to the location detection unit 190 which transfers information regarding the relative locations of the ultrasound transducer 110 and the organic specimen 160 via location data 194 to the processor 130, to the memory module 125 within which the processor 130 is coupled to the anatomic model memory 126, the ultrasound memory 127, and the extracted model memory 128, to the display module 135 within which the processor 130 is coupled to the ultrasound display 140 and the model display 145, and to the ultrasound controller 120. Coupling between the various components of the system 100 could be via electronic cables, optical fibers, pairs of radio frequencies or infrared transmitter/receivers, or other appropriate means for transmitting or transferring signals.

The ultrasound memory 127 is configured to store sets of ultrasound data 187 obtained from the ultrasound transducer 110. The anatomic model memory 126 is configured to store anatomic model data 186 which is a model of and representative of at least part 155 of an organic specimen 160. The extracted model memory 128 is configured to store sets of model extracted data 188. In representative embodiments, a set of model extracted data 188 can be obtained from the anatomic model data 186 for each set of ultrasound data 187 and can be associated with each set of ultrasound data 187. Each associated set of ultrasound data 187 and model extracted data 188 can be used to create associated ultrasound and model images 180, 185 wherein the model image 185 is a model of the region from which the ultrasound image 180 is obtained. The processor 130 is configured to obtain the appropriate set of model extracted data 188 and correlate it with its associated set of ultrasound data 187. In an alternate representative embodiment, the model image 185 can be created from the set of model extracted data 188 without storage of the model extracted data 188. And in another alternate representative embodiment, the set of ultrasound data 187 and the set of model extracted data 188 are stored jointly in a single memory which could be the ultrasound memory 127. The ultrasound image 180 can be displayed on the ultrasound display 140, and concurrently the model image 185 associated with the ultrasound image 180 can be displayed on the model display 145.

The location identification module 195 is configured to instruct the emitter device 196 to transmit location interrogation signals 192 to transducer targets 230 (see FIG. 2 and discussion therewith) on the ultrasound transducer 110 and to specimen targets 240 (see FIG. 2 and discussion therewith) on an organic specimen 160 which could be a patient 160. Upon reception of the location interrogation signals 192 by the transducer targets 230 and the specimen targets 240, the transducer targets 230 and the specimen targets 240 separately respond with location information signals 193 which can be received by the receptor device 197. Information from the location information signals 193 received by the receptor device 197 is transferred from the receptor device 197 to the location identification module 195. The location identification module 195 is further configured to extract location information for the transducer targets 230 and the specimen targets 240 from the information in the location information signals 193 and/or from the location interrogation signals 192. The extracted location information for the transducer targets 230 and the specimen targets 240 is transferred to the processor 130 as location data 194. The location data 194 can be used by the processor 130 to associate a specific set of ultrasound data 187 with the relative locations and orientations of the ultrasound transducer 110 and the organic specimen 160 for which that set of ultrasound data 187 was obtained. The location data 194 can also be used by the processor 130 to obtain a set of model extracted data 188 from the anatomic model data 186 for the region from which the set of ultrasound data 187 is obtained. This set of model extracted data 188 is thereby associated with that set of ultrasound data 187.

In representative embodiments, an operator 150 holds the ultrasound transducer 110 against, for example, a shoulder 155 of a patient 160. The patient 160 shown in FIG. 1A could more generally be any organic specimen 160 and more particularly could be a person 160, a baby 160, another animal 160, a plant 160 or the like. However, the term organic specimen 160 as used herein more generally means any living or deceased organism or any portion of a living or deceased organism. In particular, the organic specimen could be a human, another animal, a plant, a portion of a human, a portion of another animal, or a portion of a plant. The shoulder 155 shown in FIG. 1A could more generally be a part 155 of any organic specimen 160. The initiation signal 171, the activation signal 172 and reflected data signal 173 will be more completely described with the description of FIG. 2. The anatomic model data 186 stored in the memory module 125 could be anatomic model data 186 of at least part 155 of the organic specimen 160. In representative embodiments, the anatomic model data 186 could be obtained, for example, from the Visible Human Project® (VHP) or other appropriate data which can be used, for example, to create two-dimensional model images 185 of a representative human body (male or female) at diverse selected depths and angular orientations. The VHP data and other model data sources could be used to create static two-dimensional, static three-dimensional, time varying two-dimensional, and/or time varying three-dimensional model images 185. Various components of FIG. 1A will be more completely described with the description of subsequent figures.

While the representative embodiments disclosed herein are discussed in terms of static two-dimensional model and ultrasound images 185,180, the representative embodiments can also be implemented using time varying two-dimensional model and ultrasound images 185,180, static three-dimensional model and ultrasound images 185,180, and time varying three-dimensional model and ultrasound images 185,180. As appropriate, these images can be displayed, for example, on a two-dimensional display system as static or time varying two-dimensional images and on a three-dimensional display system as static or time varying three-dimensional images.

Figure 1B:
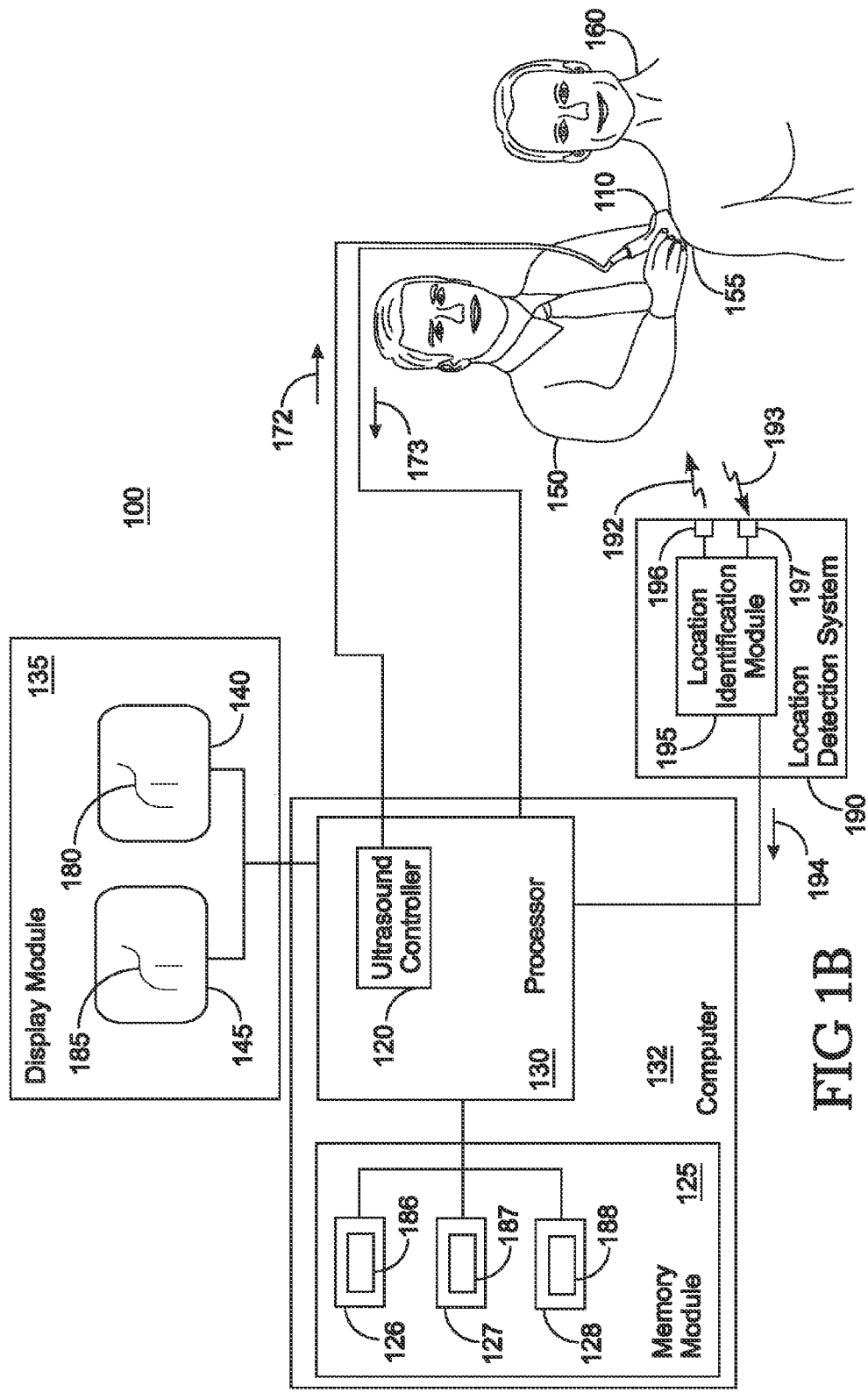
FIG. 1B is a block diagram of another system for identification of organic specimen features in ultrasound images as described in various representative embodiments.

FIG. 1B is a block diagram of another system 100 for identification of organic specimen 160 features in ultrasound images 180 as described in various representative embodiments. The system 100 of FIG. 1B differs from that of FIG. 1A by the inclusion of the functions of the ultrasound controller 120 in the processor 130. In this embodiment, the processor 130 comprises the ultrasound controller 120 which creates the activation signal 172 directly and then transfers the activation signal 172 to the ultrasound transducer 110. Again, the activation signal 172 and the reflected data signal 173 will be more completely described with the description of FIG. 2, and various other components of FIG. 1B will be more completely described with the description of subsequent figures.

FIG. 1C is a block diagram of still another system 100 for identification of organic specimen 160 features in ultrasound images 180 as described in various representative embodiments. The system 100 of FIG. 1C differs from that of FIG. 1A in that the ultrasound controller 120 receives the reflected data signal 173 from the ultrasound transducer 110 and then transfers the reflected data signal 173 to the processor 130 either as received or as appropriately modified. The system 100 of FIG. 1C also differs from that of FIG. 1A in that the functions of the location identification module 195 are included in the processor 130 with the emitter device 196 and the receptor device 197 located external to the processor 130. The location detection unit 190 comprises the emitter device 196, the receptor device 197, and the location identification module 195. Again, the activation signal 172 and the reflected data signal 173 will be more completely described with the description of FIG. 2, and various other components of FIG. 1C will be more completely described with the description of subsequent figures.

In alternative embodiments, the location detection unit 190 of FIG. 1A could replace the location detection unit 190 of FIG. 1C in the configuration of FIG. 1C, the location detection unit 190 of FIG. 1C could replace the location detection unit 190 of FIG. 1A in the configuration of FIG. 1A, and the location detection unit 190 of FIG. 1C could replace the location detection unit 190 of FIG. 1B in the configuration of FIG. 1B.

Figure 1D:
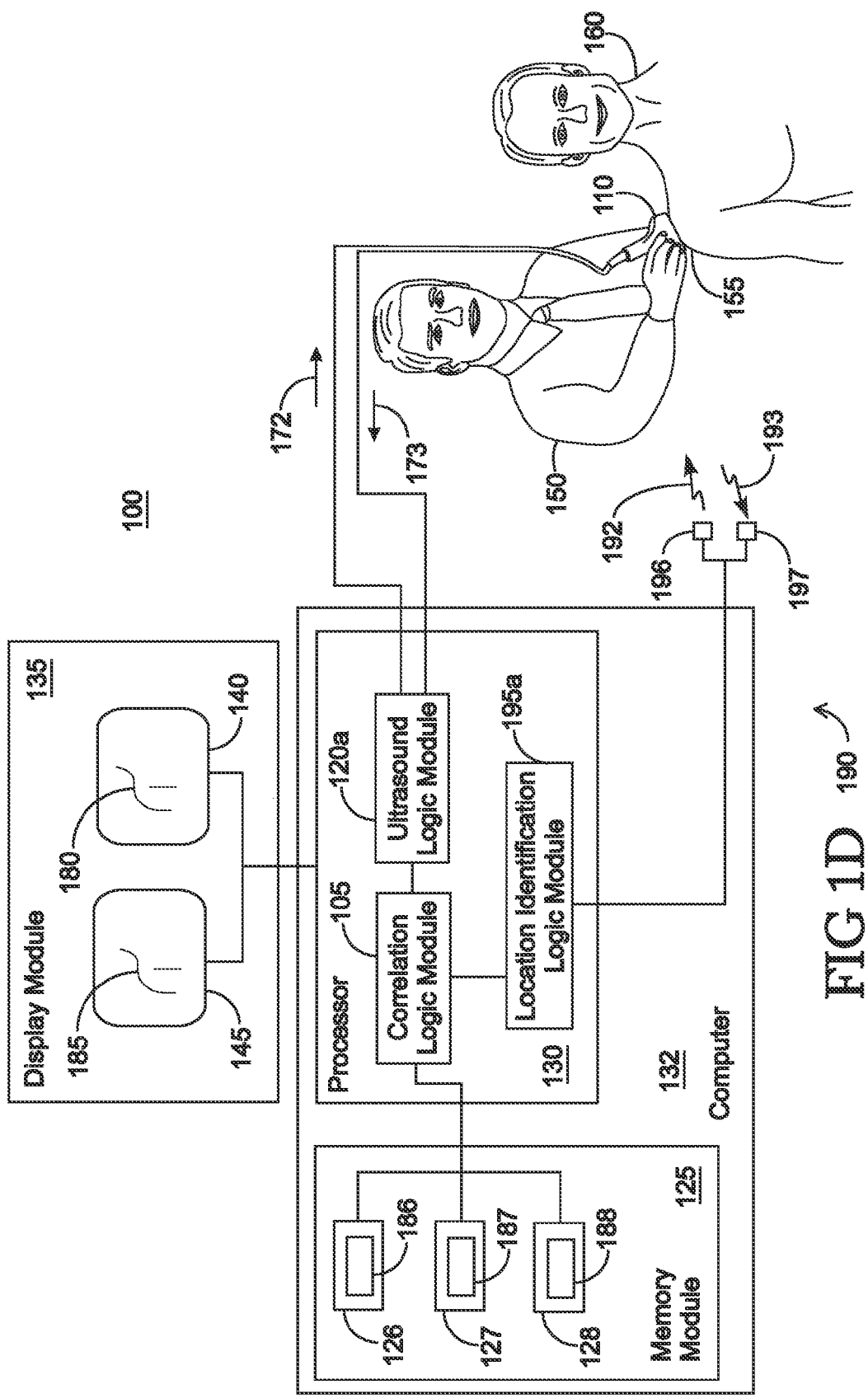
FIG. 1D is a block diagram of yet another system for identification of organic specimen features in ultrasound images as described in various representative embodiments.

FIG. 1D is a block diagram of yet another system for identification of organic specimen 160 features in ultrasound images 180 as described in various representative embodiments. The system 100 of FIG. 1D differs from that of FIG. 1A in that the processor 130 comprises an ultrasound logic module 120a, a location identification logic module 195a, and a correlation logic module 105.

The ultrasound logic module 120a can be configured to perform the functions associated with the ultrasound controller 120 of FIGS. 1A, 1B, and/or 1C and is operatively coupled to the ultrasound transducer 110 and to the correlation logic module 105. upon instructions from the processor 130, the ultrasound logic module 120a initiates transmission of the activation signal 172 to the ultrasound transducer 110 and receives the subsequent reflected data signal 173. The ultrasound logic module 120a then transfers ultrasound data 187 from the reflected data signal 173 to the correlation logic module 105.

FIG. 1E is a block diagram of yet still another system for identification of organic specimen features in ultrasound images as described in various representative embodiments. The system 100 of FIG. 1E differs from that of FIG. 1D in that the processor 130 comprises a computer program 133 which is also referred to herein as a computer program product 133.

The computer program product 133 comprises instructions for carrying out a method 900 when executed by the processor 130 on the computer 132. The computer program product 133 is stored on a computer readable storage medium which could be the memory module 125 and/or the memory of the processor 130. The computer readable storage medium could be the hard drive of a computer, a floppy disk, a CD, a DVD, a RAM memory, or other acceptable storage medium. In a representative embodiment, the computer program product 133 comprises an ultrasound logic module 120a, a location identification logic module 195a, and a correlation logic module 105. These logic modules comprise instructions for performing a method 900, wherein the method 900 comprises: specifying a reference model image region 520a in model extracted data 188 obtained from anatomic model data 186 of at least part 155 of an organic specimen 160; instructing an ultrasound transducer 110 to transmit ultrasound incident waves 201 into the organic specimen 160 and receiving thereby ultrasound data 187 from ultrasound reflected waves 202 from specimen features 210 in the organic specimen 160, wherein positional awareness 194 of each ultrasound reflected wave 202 relative to the organic specimen 160 is maintained; identifying a reference propagation region 220a corresponding to the reference model image region 520a from paired recognized specimen features 210 in the ultrasound data 202 and in the model extracted data 188; instructing the ultrasound transducer 110 to transmit at least one subsequent ultrasound incident wave 201 into the organic specimen 160 and receiving thereby subsequent ultrasound data 187 from ultrasound reflected waves 202 from one or more specimen features 210, wherein positional awareness is maintained between the reference propagation region 220a and the propagation region 220 of the subsequent ultrasound data 187; and for the subsequent ultrasound data 187, creating an ultrasound image 180, creating a model image 185 for a model image region 520 from the anatomic model data 186 corresponding to the propagation region 220 of the subsequent ultrasound data 187, and instructing a display module 135 to display the ultrasound image 180 and the model image 185.

The location identification logic module 195a is configured to instruct the emitter device 196 to transmit location interrogation signals 192 to transducer targets 230 (see FIG. 2 and discussion therewith) on the ultrasound transducer 110 and to specimen targets 240 (see FIG. 2 and discussion therewith) on an organic specimen 160 which could be a patient 160 and to receive location information from subsequent location information signals 193 received by the receptor device 197. The location identification logic module 195*a* is further configured to extract location information for the transducer targets 230 and/or the specimen targets 240 from the information in the location information signals 193 and/or from the location interrogation signals 192. This location information is then transferred to the correlation logic module 105. In FIG. 1D, the location detection unit 190 comprises the emitter device 196, the receptor device 197, and the location identification logic module 195*a*.

The correlation logic module 105 is configured to receive ultrasound data 187 from the ultrasound logic module 120*a* and location information from the location identification logic module 195*a*, to obtain model extracted data 188 from the anatomic model data 186 in the memory module 125, to identify a reference model image plane 520*a* in the model extracted data 188, to identify a corresponding reference propagation plane 220*a* from recognized specimen features 210 in the ultrasound data 187 and associated location information from the location identification logic module 195*a*, to receive ultrasound data 187 from subsequent ultrasound reflected waves 202 from one or more specimen features 210 wherein positional awareness is maintained between the reference propagation plane 220*a* and the propagation plane 220 of the subsequent ultrasound data 187, and for the subsequent ultrasound data 187 to create an ultrasound image 180, to create a model image 185 for a model image plane 520 from the anatomic model data 186 corresponding to the propagation plane 220 of the subsequent ultrasound data 187, and to transfer the ultrasound image 180 and the model image 185 to the display module 135. As appropriate, the correlation logic module 105 can be further configured to store the ultrasound data 187, the model extracted data 188, the ultrasound images 180, and/or the model images 185.

In alternative representative embodiments, the ultrasound logic module 120*a*, the location identification logic module 195*a*, and/or the correlation logic module 105 can be implemented in hardware, as a software program, or in firmware either external to or internal to the processor 130. The software program and/or the firmware could be configured to provide instructions to the computer 105 to perform various method steps and/or functions disclosed herein. In other alternative embodiments, the ultrasound logic module 120*a*, the location identification logic module 195*a*, and/or the correlation logic module 105 can be replaced respectively by the ultrasound controller 120, the location identification module 195, and or the functions of the processor 130 as in the configurations of FIGS. 1A, 1B, and/or 1C.

Figure 2:
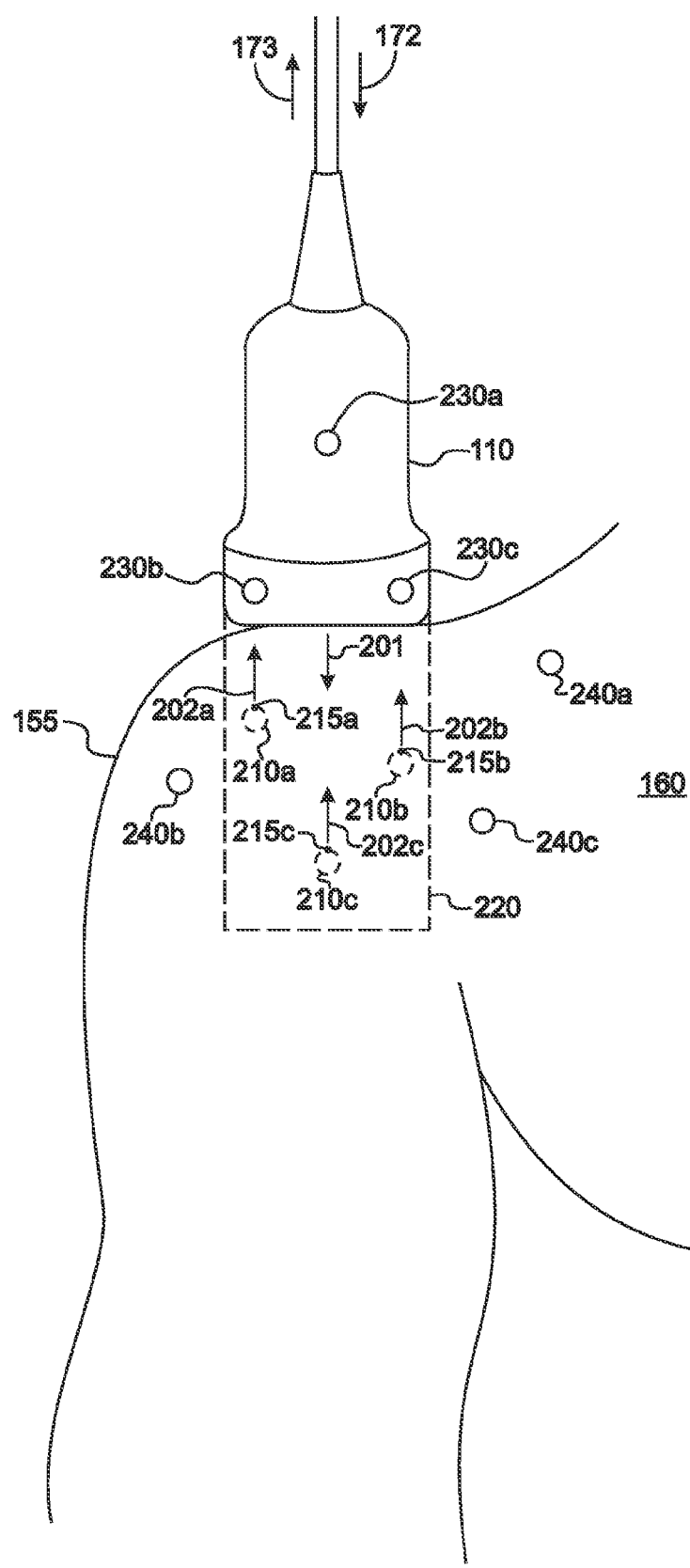
FIG. 2 is a front view of the patient of FIGS. 1A, 1B, and 1C with the ultrasound transducer coupled to the shoulder of the patient.

FIG. 2 is a front view of the patient 160 of FIGS. 1A, 1B, and 1C with the ultrasound transducer 110 coupled to the shoulder 155 of the patient 160. In the embodiment of FIG. 2, the activation signal 172 is transferred to the ultrasound transducer 110 which converts it to an ultrasound incident wave 201 and then transmits the ultrasound incident wave 201 into the shoulder 155 of the patient 160 in a propagation plane 220. The propagation plane 220 is considered in an ideal sense to extend to infinity in two dimensions. However, only that part of the propagation plane 220 into which the ultrasound incident wave 201 is transmitted is shown in FIG. 2. The ultrasound incident wave 201 is reflected by various specimen features 210, as well as patient unique features 450 (see FIG. 4 and discussion therewith) which are also referred to herein as organic specimen unique features 450, in the patient's shoulder 155 as ultrasound reflected waves 202. A patient unique feature 450 could be a pathologic feature 450 such as a muscle tear, a tendon tear such as a rotator cuff tear, a nerve problem, a blood clot in the vascular system, or the like, or it could be a foreign object 450 such as a metallic pin affixed to a broken bone in the patient 160 or the like. The ultrasound reflected waves 202 are detected by the ultrasound transducer 110 and converted into a reflected data signal 173 which is in turn transferred back to the processor 130. The plane of the ultrasound image 180 created from the reflected data signal 173 is from features in the propagation plane 220 and, thus, the propagation plane 220 is also the plane of the ultrasound image 180 and is also referred to as the ultrasound image plane 220.

The three specimen features 210*a*,210*b*,210*c* (first specimen feature 210*a*, second specimen feature 210*b*, and third specimen feature 210*c*) separately reflect that part of the ultrasound incident wave 201 incident on them as associated ultrasound reflected waves 202*a*,202*b*,202*c* (first ultrasound reflected wave 202*a*, second ultrasound reflected wave 202*b*, and third ultrasound reflected wave 202*c*). In the representative embodiment of FIG. 2, these three specimen features 210*a*,210*b*,210*c* have separately identifiable specimen reference points 215 (first specimen reference point 215*a*, second specimen reference point 215*b*, and third specimen reference point 215*c*) that together specify a reference propagation plane 220*a* which is used for specifying the location of and identification of additional, detected specimen features 210. The three specimen features 210*a*,210*b*,210*c* and their associated specimen reference points 215*a*,215*b*,215*c* in the representative embodiment of FIG. 2 are shown for illustrative purposes only and are not intended to represent any physical feature of the shoulder 155 or any other part 155 of the patient 160.

In locating the specimen reference points 215*a*,215*b*,215*c* which are typically selected previously for locating, the operator 150 moves the ultrasound transducer 110 to different locations on the shoulder 155 of the patient 160 until the three specimen reference points 215*a*,215*b*,215*c* are found. For ease of illustration and discussion, all three specimen reference points 215*a*,215*b*,215*c* are shown in FIG. 2 as being detected with the ultrasound transducer 110 in a single location, i.e., with the three specimen reference points 215*a*,215*b*, 215*c* in a single reference propagation plane 220*a*. In the more general case, however, as long as current locations of the ultrasound transducer 110 are known relative to a previous location, detection of the three specimen reference points 215*a*,215*b*,215*c* in separate propagation planes 220, i.e., with the ultrasound transducer 110 in separate locations relative to the patient 160 can be used to specify the reference propagation plane 220*a*.

Also shown in FIG. 2 are three transducer targets 230 (first transducer target 230*a*, second transducer target 230*b*, and third transducer target 230*c*) and three specimen targets 240 (first specimen target 240*a*, second specimen target 240*b*, and third specimen target 240*c*). In representative embodiments, the emitter device 196 of the location detection unit 190 transmits one or more location interrogation signals 192 which are received by the transducer targets 230 and the specimen targets 240. In response to the location interrogation signals 192, the transducer targets 230 and the specimen targets 240 return location information signals 193 which are received by the receptor device 197. The location identification module 195 monitors any movement of the ultrasound transducer 110 and of the patient 160. The location identification module 195 transfers information regarding the locations of the ultrasound transducer 110 and the organic specimen 160 via location data 194 to the processor 130. The transducer and specimen targets 230,240 could transmit location information signals 193 in response to location interrogation signals 192, actively transmit location information signals 193 automatically without initiation from the location interrogation signals 192, or passively reflect the location interrogation signals 192 as location information signals 193. The location interrogation signals 192 and location information signals 193 could be infrared, optical, radio frequency or any other acceptable signal types. In addition, information regarding the relative locations of the ultrasound transducer 110 and the organic specimen 160 can be maintained as the ultrasound transducer 110 and/or the organic specimen 160 are/is moved by a mechanical fixture (see FIG. 3) attached to the ultrasound transducer 110 or by an inertial reference device (see FIG. 4) attached to the ultrasound transducer 110.

Figure 3:
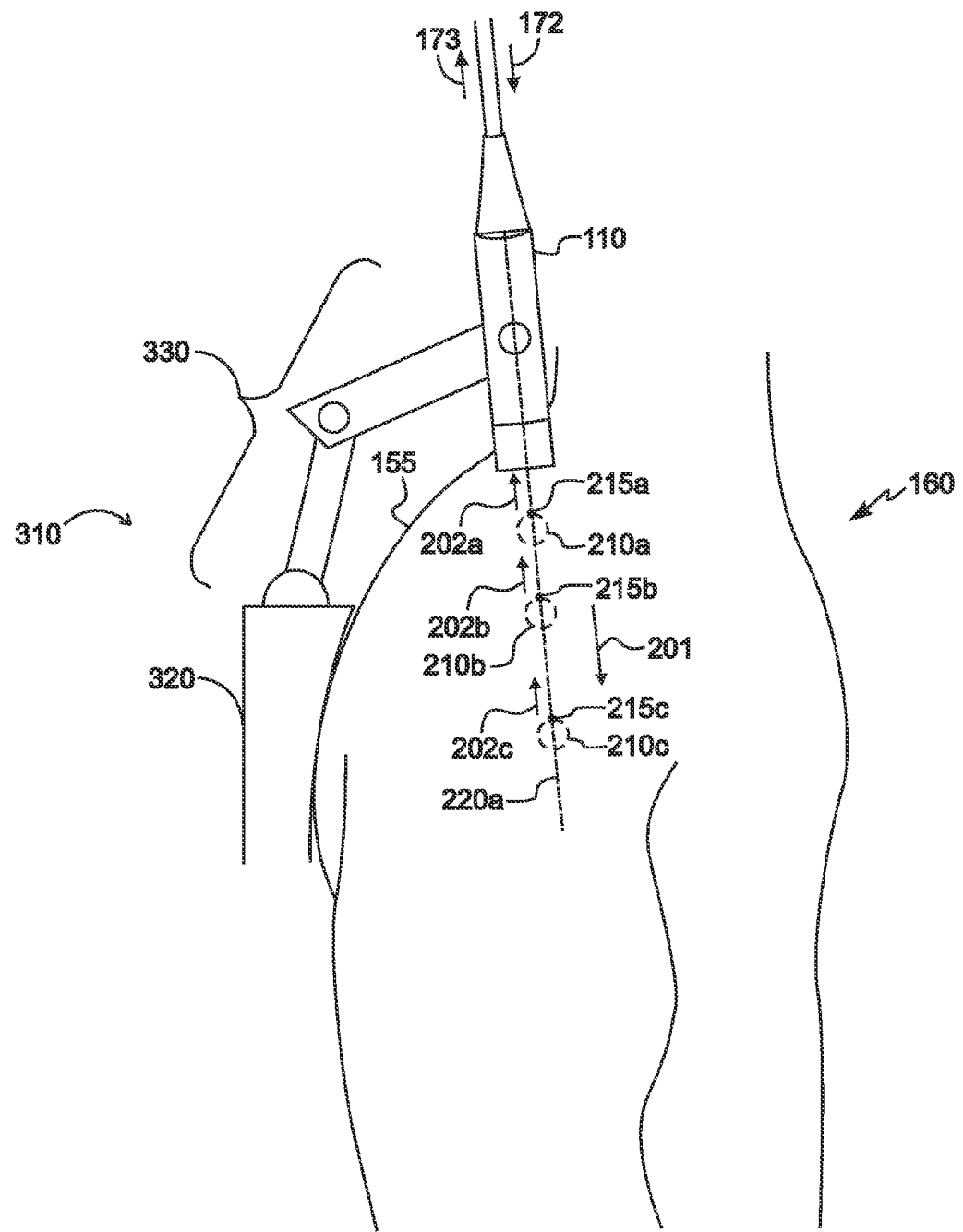
FIG. 3 is a side view of the arrangement whose front view is shown in FIG. 2.

FIG. 3 is a side view of the arrangement whose front view is shown in FIG. 2. As indicated in the discussion of FIG. 2, the three specimen features 210a,210b,210c separately reflect that part of the ultrasound incident wave 201 incident on them as associated ultrasound reflected waves 202a,202b, 202c (first ultrasound reflected wave 202a, second ultrasound reflected wave 202b, and third ultrasound reflected wave 202c). In the representative embodiment of FIGS. 2 and 3, these three specimen features 210a,210b,210c have separately identifiable specimen reference points 215a,215b,215c that together specify a reference propagation plane 220a that will be used for specifying the location of and identification of additional, detected specimen features 210. The reference propagation plane 220a of the ultrasound incident wave 201 is shown edge on in FIG. 3 and therefore appears as a line in that figure. As previously indicated, all three specimen reference points 215a,215b,215c may be detected with the ultrasound transducer 110 in a single location as shown in FIGS. 2 and 3. However, as long as any current location of the ultrasound transducer 110 is known relative to a previous location, the three specimen reference points 215a,215b,215c can be detected in separate propagation planes 220, i.e., with the ultrasound transducer 110 in separate locations.

Also, shown in FIG. 3 is a representative embodiment wherein the emitter device 196 and the receptor device 197 of the location detection unit 190 are replaced by a mechanical coupling device 310 which can be used to maintain a reference between the location of the ultrasound transducer 110 and the location of the patient 160. The mechanical coupling device 310 comprises a mechanical fixture 320 and a mechanical coupler 330. In order to reduce or eliminate movement by the patient 160, the mechanical fixture 320 is placed adjacent to the patient 160. The mechanical coupler 330 is located between the mechanical fixture 320 and the ultrasound transducer 110. Measurements of various angular rotations of components in the mechanical coupling device 310 relative to the reference propagation plane 220a can be used to compute the new propagation plane 220 following any movement of the ultrasound transducer 110.

Figure 4:
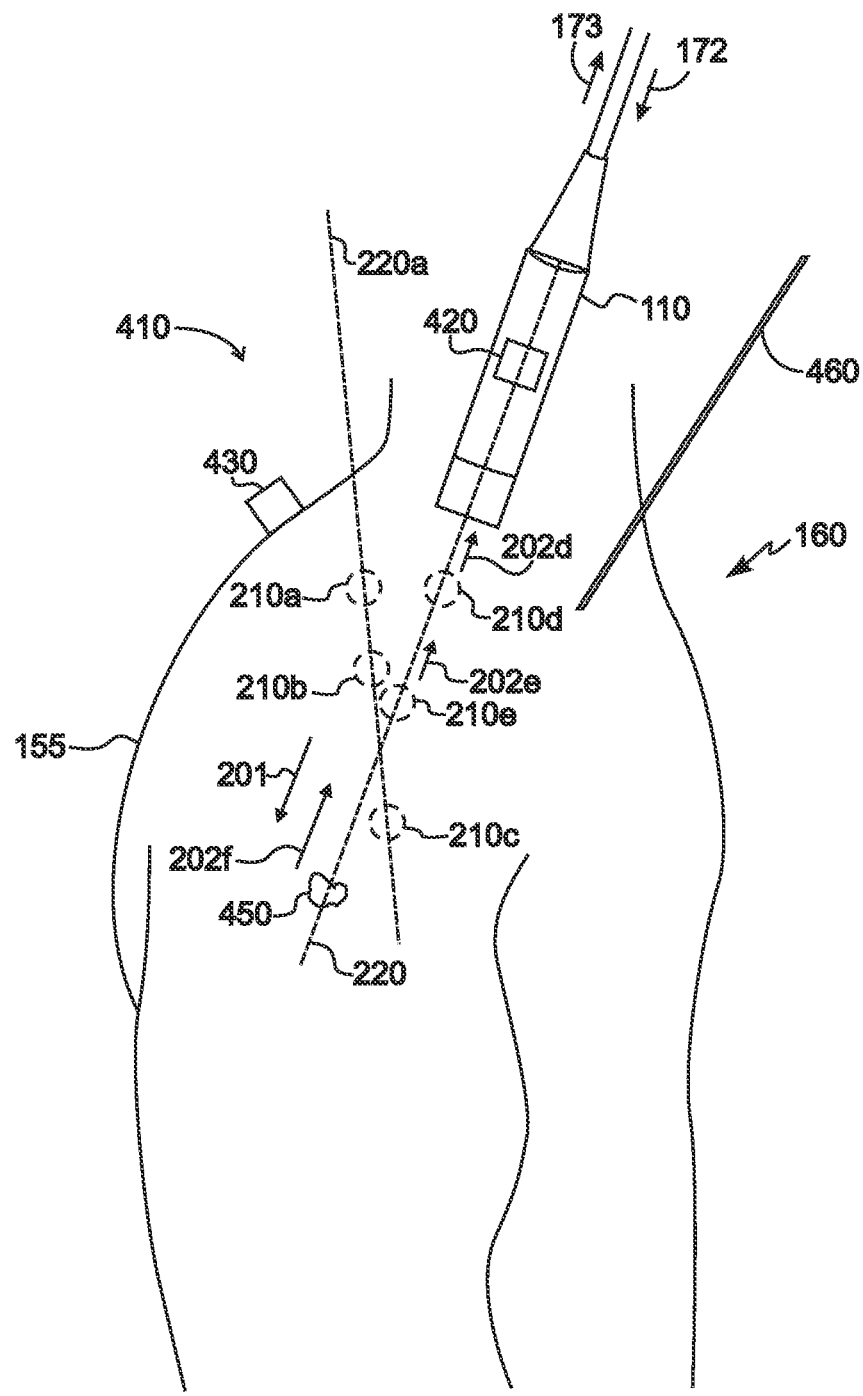
FIG. 4 is a side view of a modified arrangement of the side view shown in FIG. 3.

FIG. 4 is a side view of a modified arrangement of the side view shown in FIG. 3. In FIG. 4, the ultrasound transducer 110 is again coupled to the shoulder 155 of the patient 160. However, the ultrasound transducer 110 has been moved to another location on the shoulder 155 of the patient 160.

Also, shown in FIG. 4 is a representative embodiment wherein the emitter device 196 and the receptor device 197 of the location detection unit 190 of FIGS. 1A, 1B, and 1C are replaced by an inertial reference device 410 which can be used to maintain a reference between the location of the ultrasound transducer 110 and the location of the patient 160. The inertial reference device 410 comprises a first inertial module 420 and a second inertial module 430. The first inertial module 420 is coupled to the ultrasound transducer 110 and a second inertial module 430 is coupled to the patient 160. Communication between the first and the second inertial modules 420,430 and the processor 130 can be effected by infrared, optical, radio frequency, or any other acceptable communication technology. A combination of the mechanical fixture 320 in FIG. 3 coupled to the patient 160 and the first inertial module 420 coupled to the ultrasound transducer 110 can also be used to maintain information regarding the location of the ultrasound transducer 110 relative to the patient 160.

As previously discussed, the ultrasound transducer 110 converts the activation signal 172 to an ultrasound incident wave 201 and transmits it into the shoulder 155 of the patient 160 in the propagation plane 220. The ultrasound incident wave 201 in FIG. 4 is reflected in the patient's shoulder 155 by two additional specimen features 210d,210e (fourth specimen feature 210d and fifth specimen feature 210e) and the patient unique feature 450 as additional ultrasound reflected waves 202d,202e,202f (fourth ultrasound reflected wave 202d, fifth ultrasound reflected wave 202e, and sixth ultrasound reflected wave 202f). The ultrasound reflected waves 202d,202e,202f are detected by the ultrasound transducer 110 and converted into the reflected data signal 173. However, the three specimen features 210a,210b,210c and their associated specimen reference points 215a,215b,215c are not detectable by the ultrasound transducer 110 with the ultrasound transducer 110 positioned as in FIG. 4 as these specimen features 210a,210b,210c do not lie in the current propagation plane 220.

Also in FIG. 4 is an instrument 460 shown inserted into the patient's 160 shoulder 155. The placement of the instrument 460 within the patient's 160 shoulder 155 can be adjusted using appropriate ultrasound transducer 110 positions and the resultant displayed ultrasound and model images 180,185. The instrument 460 can be configured for providing medical treatment to the patient 160 or for obtaining diagnostic information regarding the patient 160 such as obtaining a biopsy.

Figure 5:
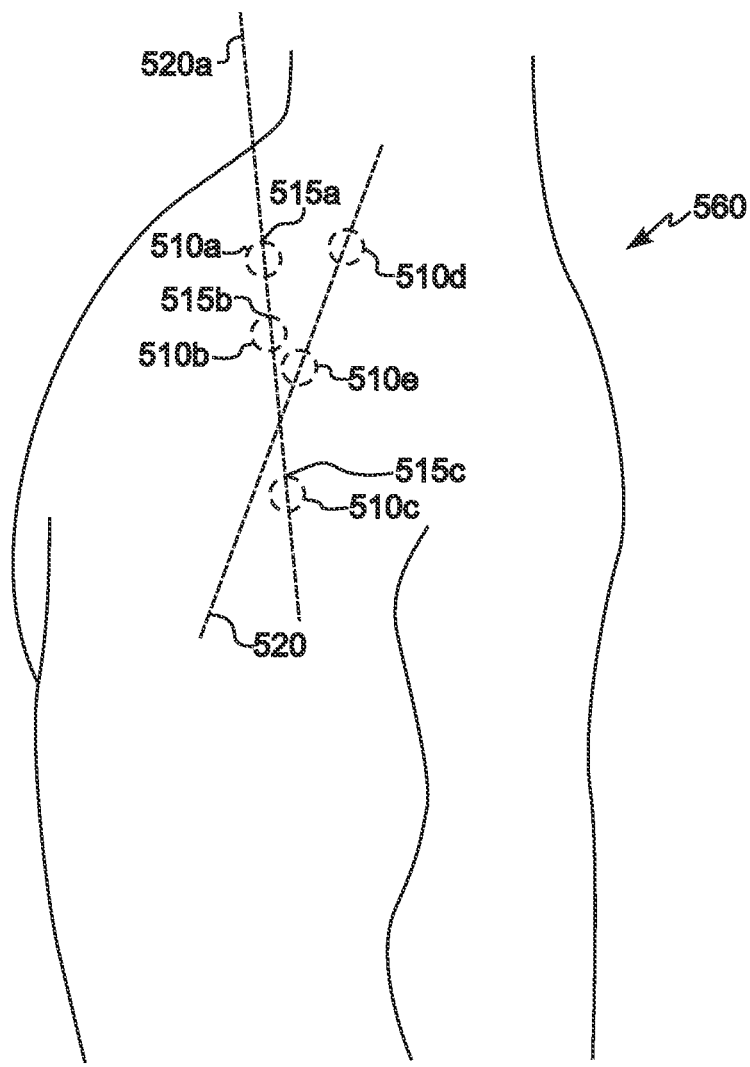
FIG. 5 is a side view of a three-dimensional reconstructed model from the anatomic model data for the arrangement of FIG. 4.

FIG. 5 is a side view of a three-dimensional reconstructed model 560 from the anatomic model data 186 for the arrangement of FIG. 4. In FIG. 5 are shown a first, a second, a third, a fourth, and a fifth model features 510a,510b,510c,510d, 510e that in order correspond to the first, the second, the third, the fourth, and the fifth specimen features 210a,210b,210c, 210d,210e and a first, a second, and a third model reference points 515a,515b,515c that in order correspond to the first, the second, and the third specimen reference points 215a, 215b,215c shown in FIG. 4. Also shown in FIG. 5 is a model image plane 520 that corresponds to the propagation plane 220 (the ultrasound image plane 220) of FIG. 4. Note that the first, the second, and the third model features 510a,510b,510c and their associated first, second, and third model reference points 515a,515b,515c lie in another model image plane 520a referred to herein as the reference model image plane 520a. The reference model image plane 520a for the model image 185 that includes the first, second, and third model reference points 515a,515b,515c corresponds to the reference ultrasound image plane 220a for the ultrasound image 180 that includes the first, second, and third specimen reference points 215a,215b,215c. Note also, that FIG. 5 does not include a model feature 510 that corresponds to the patient unique feature 450 as such items are not a part of the anatomic model data 186.

Figure 6:
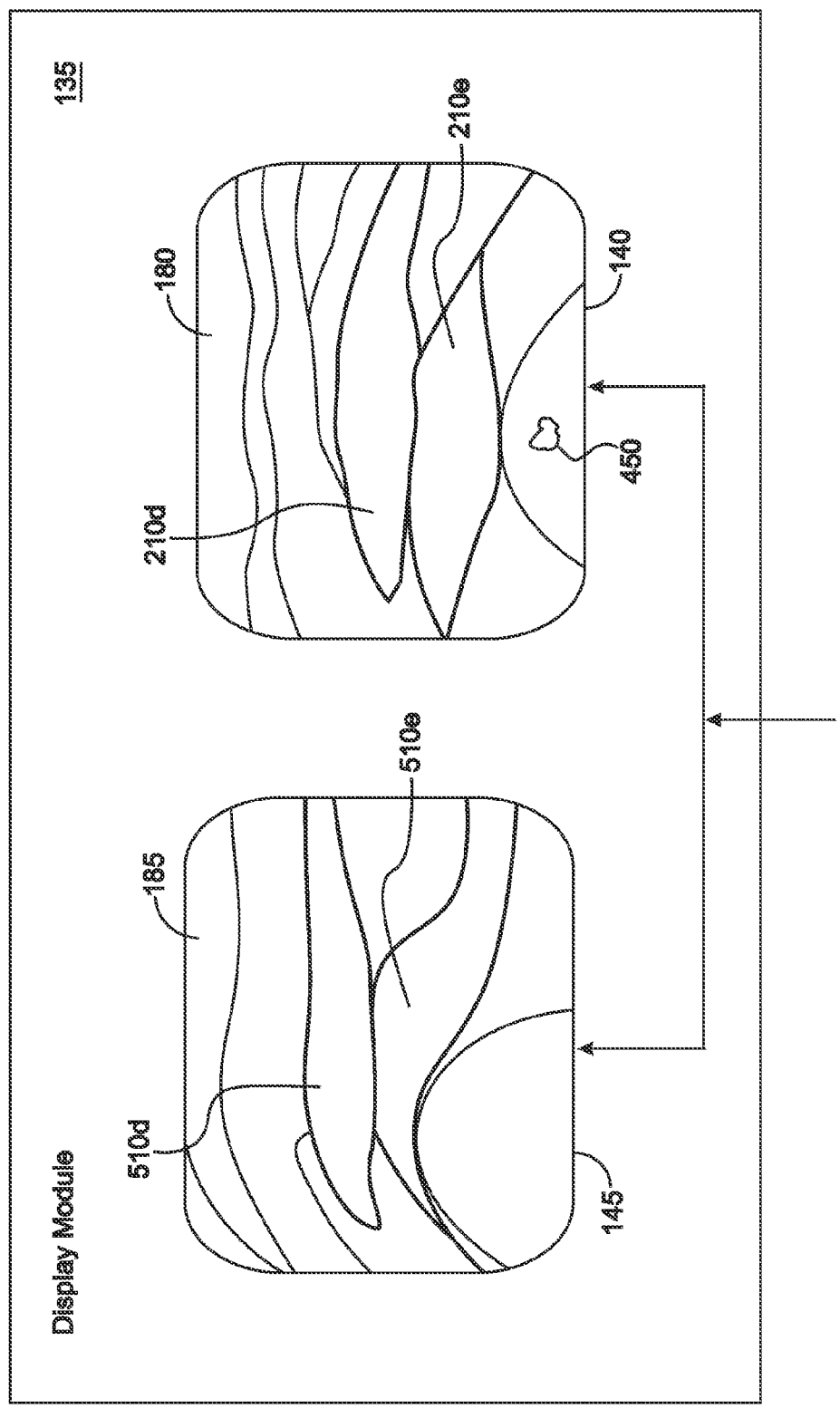
FIG. 6 is another drawing of the display module of FIGS. 1A, 1B, and 1C with the ultrasound transducer placed as in FIG. 4.

FIG. 6 is another drawing of the display module 135 of FIGS. 1A, 1B, and 1C with the ultrasound transducer 110 placed as in FIG. 4. In FIG. 6, as in FIGS. 1A, 1B, and 1C, the ultrasound image 180 is displayed on the ultrasound display 140 and a corresponding model image 185 is preferably displayed concurrently on the model display 145. The model image 185 is a display of a two-dimensional slice through a representative model of the patient 160 for a plane that corresponds to the propagation plane 220 of the ultrasound incident wave 201 shown in FIG. 4. The ultrasound reflection of the fourth and the fifth specimen features 210d,210e and the patient unique feature 450 of the ultrasound image 180 of the patient's shoulder 155 are indicated on the ultrasound display 140, and the corresponding model features 510 (fourth model feature 510d and fifth model feature 510ec) are shown on the model image 185 displayed on the model display 145.

Other locations of the ultrasound transducer 110 will result in displayed ultrasound and model images 180,185 for other propagation planes 220. A set of ultrasound data 187 for the ultrasound image 180 can be stored for future reference and future creation of ultrasound images 180 in the ultrasound memory 127 of the memory module 125. The stored set of ultrasound data 187 can be keyed to or stored with a set of model extracted data 188 obtained from the anatomic model data 186 for the region of that part 155 of the patient 160 from which the ultrasound data 187 was obtained.

The two specimen features 210d,210e, the patient unique feature 450, and the two model features 510d,510e in FIG. 6 are shown for illustrative purposes only and are not intended to represent any particular feature 210 or patient unique feature 450 in the shoulder 155 or any other part 155 of the patient 160.

Figure 7:
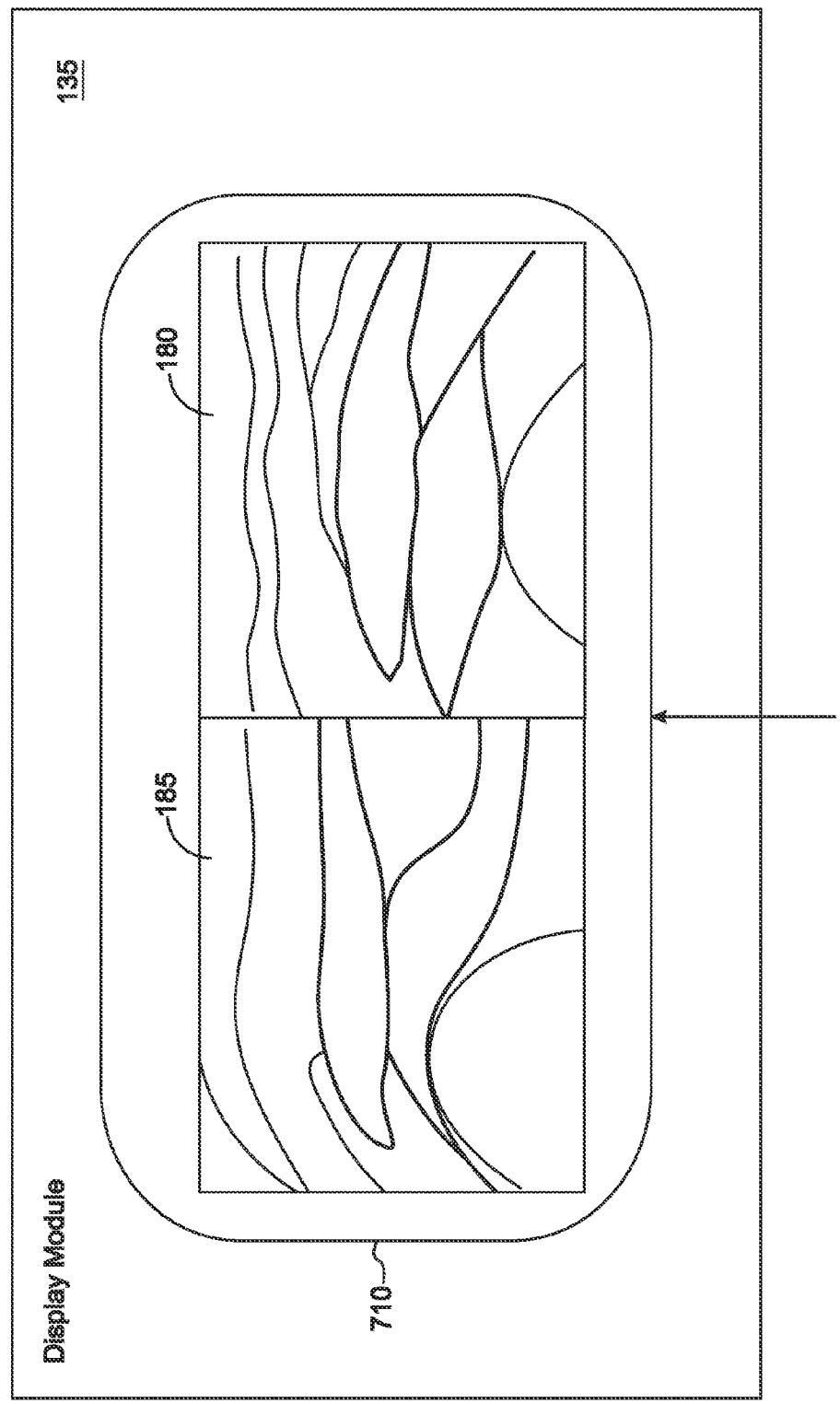
FIG. 7 is a drawing of an alternative embodiment of a display module for the systems of FIGS. 1A, 1B, and 1C.

FIG. 7 is a drawing of an alternative embodiment of a display module 135 for the systems 100 of FIGS. 1A, 1B, and 1C. The display module 135 of FIG. 7 comprises a single display 710 in a split screen mode for the combined display of the ultrasound image 180 and the model image 185. For ease and clarity of illustration, the two specimen features 210d, 210e and the patient unique feature 450 as well as the corresponding two model features 510d,510e are not labeled in FIG. 7 as they were in FIG. 6.

As in FIG. 6, other locations of the ultrasound transducer 110 will result in displayed ultrasound and model images 180,185 for other propagation planes 220. A set of ultrasound data 187 for the ultrasound image 180 can be stored for future reference and future creation of ultrasound images 180 in the ultrasound memory 127 of the memory module 125. The stored set of ultrasound data 187 can be keyed to or stored with a set of model extracted data 188 obtained from the anatomic model data 186 for the region of that part 155 of the patient 160 from which the ultrasound data 187 was obtained.

Figure 8:
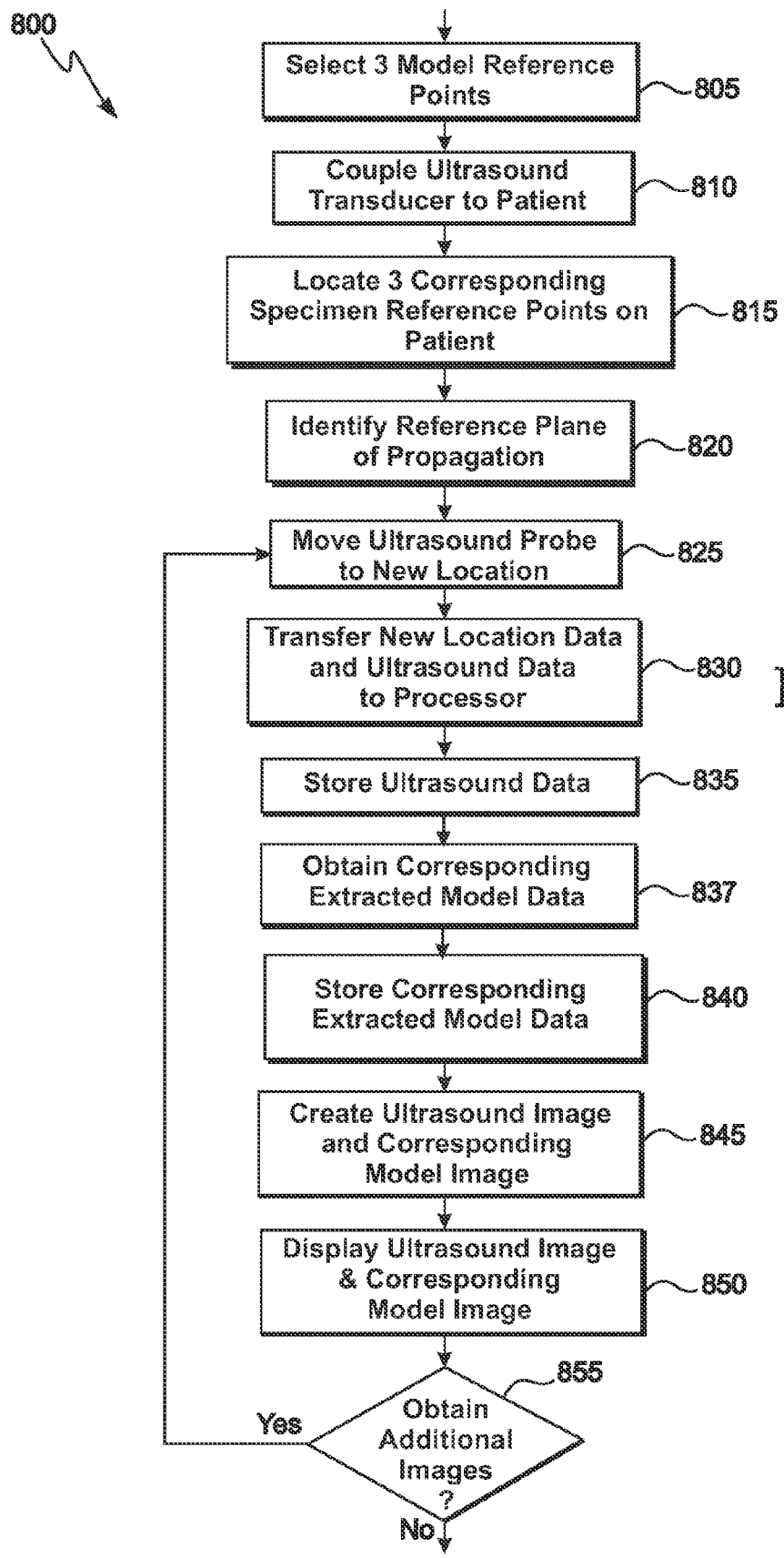
FIG. 8 is a flow chart of a method for the identification of organic specimen features in ultrasound images as described in various representative embodiments.

FIG. 8 is a flow chart of a method 800 for the identification of organic specimen 160 features 210 in ultrasound images 180 as described in various representative embodiments. In block 805 of FIG. 8, three model reference points 515 (first, second, and third model reference points 515a,515b,515c) are selected. Block 805 then transfers control to block 810.

In block 810, the ultrasound transducer 110 is coupled to the organic specimen 160 which could be, for example, the patient 160. Block 810 then transfers control to block 815.

In block 815, the ultrasound transducer 110 is moved until the three specimen reference points 215 (first, second, and third specimen reference points 215a,215b,215c) on the patient 160 that correspond to the three model reference points 515 (first, second, and third model reference points 515a,515b,515c) are located and marked on the ultrasound data 187. Block 815 then transfers control to block 820.

In block 820, the reference propagation plane 220a is identified based on the first, the second, and the third specimen reference points 215a,215b,215c. Block 820 then transfers control to block 825.

In block 825, the ultrasound transducer 110 is moved to a new location on the patient 160. Block 825 then transfers control to block 830.

In block 830, data specifying the new location of the ultrasound transducer 110 is transferred by the location detection unit 190 to the processor 130, and the reflected data signal 173 is transferred to the processor 130 from which a set of ultrasound data 187 is obtained. Block 830 then transfers control to block 835.

In block 835, the set of ultrasound data 187 is stored in the ultrasound memory 127. Block 835 then transfers control to block 837.

In block 837, a set of model extracted data 188 is obtained from the anatomic model data 186 in the anatomic model memory 126 for the region from which the set of ultrasound data 187 is obtained. Block 837 then transfers control to block 840.

In block 840, the corresponding set of model extracted data 188 is stored in the extracted model memory 128. Block 840 then transfers control to block 845.

In block 845, an ultrasound image 180 is created from the set of ultrasound data 187, and a corresponding model image 185 is created from the associated set of model extracted data 188. Block 845 then transfers control to block 850.

In block 850, the ultrasound image 180 and the corresponding model image 185 are displayed on the display module 135. Block 850 then transfers control to block 855.

In block 855, if an additional ultrasound image 180 and corresponding model image 185 are to be obtained, block 855 transfers control back to block 825. Otherwise, block 855 terminates the process.

Figure 9:
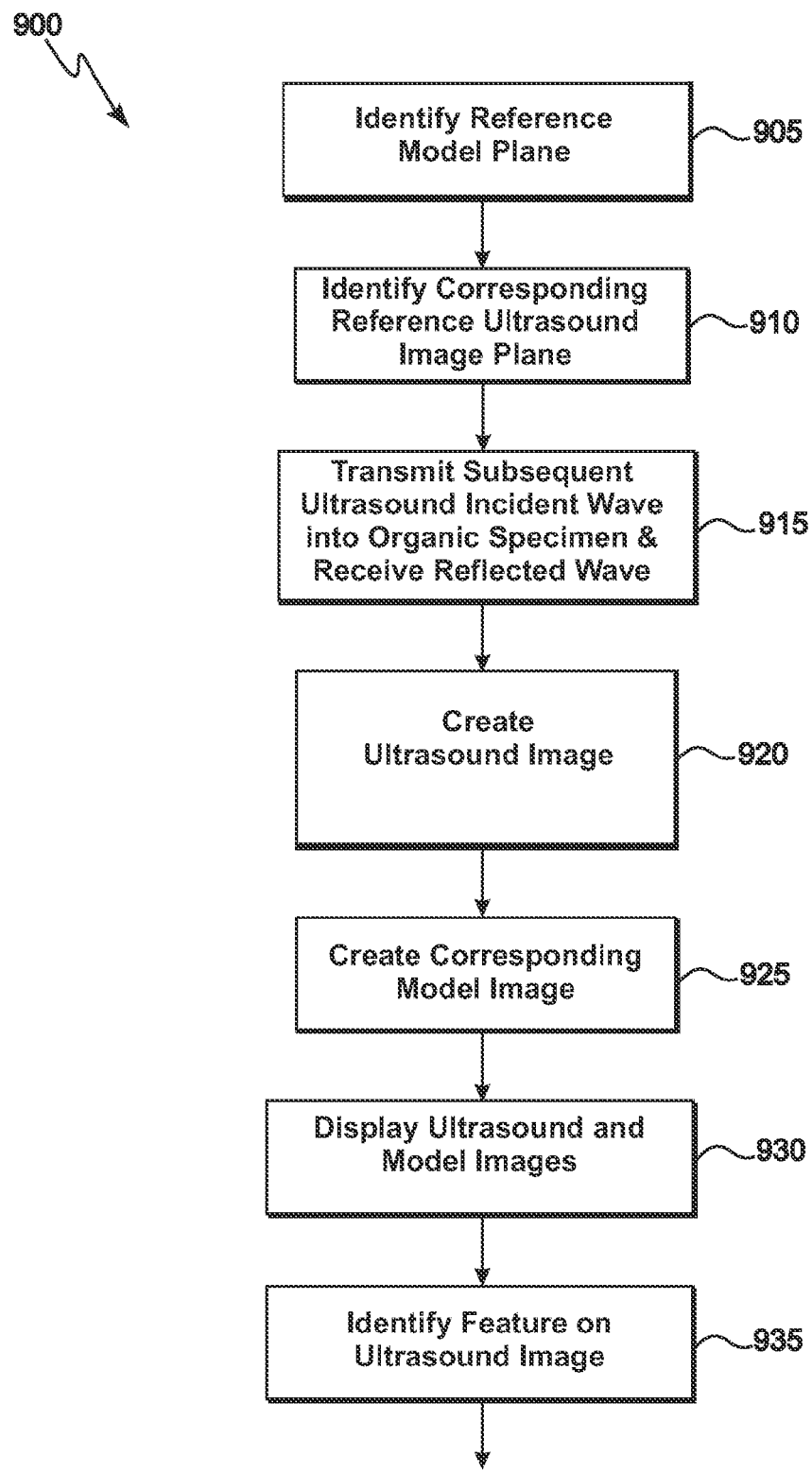
FIG. 9 is a flow chart of another method for the identification of organic specimen features in ultrasound images as described in various representative embodiments.

FIG. 9 is a flow chart of another method 900 for the identification of organic specimen 160 features 210 in ultrasound images 180 as described in various representative embodiments. In block 905 of FIG. 9, a reference model image plane 520a in anatomic model data 186 of at least a part 155 of an organic specimen 160 is identified. Block 905 then transfers control to block 910.

In block 910, a corresponding reference ultrasound image plane 220a is identified by transmitting one or more ultrasound incident waves 201 into the organic specimen 160 and receiving corresponding one or more ultrasound reflected waves 202. Positional awareness is maintained between the one or more ultrasound reflected waves 202. Block 910 then transfers control to block 915.

In block 915, at least one subsequent ultrasound incident wave 201 is transmitted into the organic specimen 160 and at least one corresponding subsequent ultrasound reflected wave 202 reflected from one or more specimen features 210 in the organic specimen 160 is received. Positional awareness is maintained between the reference ultrasound plane 220a and a propagation plane 220 of the at least one subsequent ultrasound incident wave 201. Block 915 then transfers control to block 920.

In block 920, for at least one subsequent ultrasound reflected wave 202, an ultrasound image 180, is created therefrom. Block 920 then transfers control to block 925.

In block 925, for the at least one subsequent ultrasound reflected wave 202, a corresponding model image 185 from the anatomic model data 186 for the model image plane 520 that corresponds to the ultrasound image plane 220 for the at least one subsequent ultrasound reflected wave 202 is created. Block 925 then transfers control to block 930.

In block 930, for the at least one subsequent ultrasound reflected wave 202, the ultrasound image 180 and the model image 185 are displayed on a display module 135. Block 930 then transfers control to block 935.

In block 935, for the at least one subsequent ultrasound reflected wave 202, a specimen feature 210 on the ultrasound image 180 is identified from a corresponding model feature 510 on the model image 185. Block 935 then terminates the process.

While the representative embodiments disclosed herein have been discussed in terms of the ultrasound transducer 110 coupled to the shoulder 155 of a human patient 160, it will be understood by one of ordinary skill in the art that other representative embodiments can be implemented for use with other parts 155 of any organic specimen 160. As stated above, an organic specimen 160 is any living or deceased organism or any portion of a living or deceased organism. In particular, the organic specimen could be a human, another animal, a plant, or a portion of a human, another animal, or a plant.

In representative embodiments, the ultrasound images 180 and/or the model images 185 could be stored in the memory module 125.

In alternative representative embodiments, the ultrasound controller 120 could be implemented in hardware, as a software program, or in firmware either external to or internal to the processor 130. In alternative representative embodiments, the location identification module 195 could be implemented in hardware, as a software program, or in firmware either external to or internal to the processor 130.

In other representative embodiments, the propagation plane 220 could be adjusted electronically rather than by a physical movement of the ultrasound transducer 110 relative to the organic specimen 160.

The term region as used herein refers to a plane or slice for two-dimensional embodiments and to a volume for three-dimensional embodiments. Generally for both two-dimensional and three-dimensional embodiments, the propagation plane 220 is referred to as the propagation region 220, the ultrasound image plane 220 is referred to as the ultrasound image region 220, the reference propagation plane 220a is referred to as the reference propagation region 220a, and the reference ultrasound image plane 220a is referred to as the reference ultrasound image region 220a. Also generally for both two-dimensional and three-dimensional embodiments, the model image plane 520 and the reference model image plane 520a are referred to respectively as the model image region 520 and the reference model region 520a.

The anatomic model data 186 could be obtained from data sets such as or similar to the Visible Human Project® (VHP) which can be used to create model images 185 of a representative human body (male or female) at diverse selected depths and angular orientations. The anatomic model data 186 could also be based on a theoretical model of an organic specimen 160. The anatomic model data 186 stored in the memory module 125 can be anatomic model data 186 of at least part 155 of the organic specimen 160. The processor 130 could be a central processing unit (CPU) 130 and could be located in a computer. The memory module 125 could be a computer memory 125.

In addition, while representative embodiments herein have been discussed in terms of creating and displaying static, two-dimensional ultrasound images 180, the ultrasound images 180 could also be static, three-dimensional ultrasound images 180, time varying, two-dimensional ultrasound images 180, and time varying, three-dimensional ultrasound images 180. Further, while representative embodiments herein have been discussed in terms of creating and displaying corresponding static, two-dimensional model images 185, the corresponding model images 185 could also be static, three-dimensional model images 185, time varying, two-dimensional model images 185, and time varying, three-dimensional model images 185.

Also, while representative embodiments disclosed herein have been discussed in terms of the various modules, components, and functions being located on or operatively coupled to a single processor 130, multiple processors 130 can instead be employed. And further, while representative embodiments disclosed herein have been discussed in terms of the various modules, components, and functions being located locally, at least one of these can instead be distributed.

In a first representative embodiment, a system is disclosed. The system comprises an ultrasound transducer 110 configured for transmitting ultrasound incident waves 201 into selected regions 220 of an organic specimen 160, detecting resultant ultrasound reflected waves 202 from specimen features 210 of the organic specimen 160, and transferring ultrasound data 187 in the resultant ultrasound reflected waves 202 for each of multiple selected ultrasound incident waves 201 to a processor 130; a location detection unit 190 configured for detecting locations of the ultrasound transducer 110 and the organic specimen 160 and for transferring that location data 194 to the processor 130; a memory module 125 configured for storing anatomic model data 186 for at least part 155 of the organic specimen 160; the processor 130 configured for identifying the region 220 associated with selected ultrasound data 187 using location data 194 and one or more sets of ultrasound data 187 resultant from reflections of recognized specimen features 210, creating an ultrasound image 180 from the selected ultrasound data 187, obtaining model extracted data 188 from the anatomic model data 186 corresponding to that of the selected ultrasound data 187 region 220, creating a model image 185 from that model extracted data 188, and transferring the ultrasound image 180 and the model image 185 to a display module 135; and the display module 135 configured for displaying the ultrasound image 180 and the model image 185.

In an optional aspect of the first representative embodiment, wherein the memory module 125 is further configured for storing the model extracted data 188.

In an optional aspect of the first representative embodiment, wherein the memory module 125 is further configured for storing the ultrasound data 187.

In an optional aspect of the first representative embodiment, wherein the processor 130 is configured for creating and the display module 135 is configured for displaying at least one static, two-dimensional ultrasound image 180 and its associated static, two-dimensional model image 185, and/or at least one static, three-dimensional ultrasound image 180 and its associated static, three-dimensional model image 185, and/or at least one set of time varying, two-dimensional ultrasound images 180 and its associated set of time varying, two-dimensional model images 185, and/or at least one set of time varying, three-dimensional ultrasound images 180 and its associated set of time varying, three-dimensional model images 185.

In an optional aspect of the first representative embodiment, wherein the processor 130 is a central processing unit 130.

In an optional aspect of the first representative embodiment, wherein the display module 135 comprises a first display 140 and a second display 145 and wherein the ultrasound image 180 is displayed on the first display 140 and the model image 185 is displayed on the second display 145.

In an optional aspect of the first representative embodiment, wherein the ultrasound image 180 and the model image 185 are overlaid on the display module 135 or wherein the ultrasound image 180 and the model image 185 are displayed side-by-side on the display module 135.

In an optional aspect of the first representative embodiment, wherein the model image 185 and the ultrasound image 180 are scaled to each other.

In an optional aspect of the first representative embodiment, wherein the anatomic model data 186 is obtained from the Visible Human Project data 186 for a representative human male or a representative human female.

In an optional aspect of the first representative embodiment, wherein the anatomic model data 186 is of a representative human male or a representative human female.

In an optional aspect of the first representative embodiment, wherein the resultant ultrasound reflected wave 202 further comprises reflections from a patient unique feature 450 in the organic specimen 160.

In an optional aspect of the first representative embodiment, wherein the resultant ultrasound reflected wave 202 further comprises reflections from an instrument 460 inserted into the organic specimen 160 when the ultrasound transducer 110 is appropriately located.

In an optional aspect of the first representative embodiment, wherein the resultant ultrasound reflected wave 202 further comprises reflections from an instrument 460 inserted into the organic specimen 160 when the ultrasound transducer 110 is appropriately located and wherein the instrument 460 is configured for providing medical treatment to the organic specimen 160 or is configured for providing diagnostic information regarding the organic specimen 160.

In a second representative embodiment, a method is disclosed. The method comprises specifying a reference model image region 520a in model extracted data 188 obtained from anatomic model data 186 of at least part 155 of an organic specimen 160; transmitting ultrasound incident waves 201 into the organic specimen 160 and receiving thereby ultrasound data 187 from ultrasound reflected waves 202 from specimen features 210 in the organic specimen 160, wherein positional awareness 194 of each ultrasound reflected wave 202 relative to the organic specimen 160 is maintained; identifying a reference propagation region 220a corresponding to the reference model image region 520a from paired recognized specimen features 210 in the ultrasound data 202 and in the model extracted data 188; transmitting at least one subsequent ultrasound incident wave 201 into the organic specimen 160 and receiving thereby subsequent ultrasound data 187 from ultrasound reflected waves 202 from one or more specimen features 210, wherein positional awareness is maintained between the reference propagation region 220a and the propagation region 220 of the subsequent ultrasound data 187; and for the subsequent ultrasound data 187, creating an ultrasound image 180, creating a model image 185 for a model image region 520 from the anatomic model data 186 corresponding to the propagation region 220 of the subsequent ultrasound data 187, and displaying the ultrasound image 180 and the model image 185 on a display module 135.

In an optional aspect of the second representative embodiment, the method 900 further comprises identifying at least one specimen feature 210 on the ultrasound image 180 from a corresponding model feature 510 on the model image 185.

In an optional aspect of the second representative embodiment, wherein the reference model image region 520a is a plane 520a and is specified by three non-collinear model reference points 515a,515b,515c in the anatomic model data 186 of at least part 155 of the organic specimen 160.

In an optional aspect of the second representative embodiment, wherein the reference model image region 520a is a plane 520a and is specified by three non-collinear model reference points 515a,515b,515c in the anatomic model data 186 of at least part 155 of the organic specimen 160 and wherein the reference propagation region 220a in the organic specimen 160 is a plane 220a corresponding to the reference model image plane 520a and is identified when one or more ultrasound incident waves 201 are reflected separately or in combination from three specimen reference points 215a, 215b,215c corresponding to the three model reference points 515a,515b,515c.

In an optional aspect of the second representative embodiment, wherein the model extracted data 188 is stored in a memory module 125.

In an optional aspect of the second representative embodiment, wherein the ultrasound data 187 is stored in a memory module 125.

In an optional aspect of the second representative embodiment, wherein displaying the ultrasound image 180 and the model image 185 on the display module 135 comprises: displaying at least one static, two-dimensional ultrasound image 180 and its associated static, two-dimensional model image 185, and/or displaying at least one static, three-dimensional ultrasound image 180 and its associated static, three-dimensional model image 185, and/or displaying at least one set of time varying, two-dimensional ultrasound images 180 and its associated set of time varying, two-dimensional model images 185, and/or displaying at least one set of time varying, three-dimensional ultrasound images 180 and its associated set of time varying, three-dimensional model images 185.

In an optional aspect of the second representative embodiment, wherein the anatomic model data 186 is stored in a memory module 125.

In an optional aspect of the second representative embodiment, wherein the display module 135 comprises a first display 140 and a second display 145 and wherein the ultrasound image 180 is displayed on the first display 140 and the model image 185 is displayed on the second display 145.

In an optional aspect of the second representative embodiment, wherein the ultrasound image 180 and the model image 185 are overlaid on the display module 135 or wherein the ultrasound image 180 and the model image 185 are displayed side-by-side on the display module 135.

In an optional aspect of the second representative embodiment, wherein the model image 185 and the ultrasound image 180 are scaled to each other.

In an optional aspect of the second representative embodiment, wherein the anatomic model data 186 is obtained from the Visible Human Project data 186 for a representative human male or a representative human female.

In an optional aspect of the second representative embodiment, wherein the anatomic model data 186 is for a representative human male or a representative human female.

In an optional aspect of the second representative embodiment, further comprising: detecting a patient unique feature 450 in the organic specimen 160.

In an optional aspect of the second representative embodiment, further comprising: inserting an instrument 460 into the organic specimen 160; and adjusting the instrument 460 position within the organic specimen 160 using the displayed ultrasound image 180 and displayed model image 185.

In an optional aspect of the second representative embodiment, further comprising: inserting an instrument 460 into the organic specimen 160; and adjusting the instrument 460 position within the organic specimen 160 using the displayed ultrasound image 180 and displayed model image 185, wherein the instrument 460 is configured for providing medical treatment to the organic specimen 160 or is configured for providing diagnostic information regarding the organic specimen 160.

In a third representative embodiment, a means 100 for identification of an organic specimen 160 feature 210 in an ultrasound image 180 is disclosed. The means comprises an ultrasound means 110 for transmitting ultrasound incident waves 201 into selected regions 210 of an organic specimen 160, detecting resultant ultrasound reflected waves 202 from specimen features 210 of the organic specimen 160, and transferring ultrasound data 187 in the resultant ultrasound reflected waves 202 for each of multiple selected ultrasound incident waves 201 to a processor means 130; a location detection means 190 for detecting locations of the ultrasound means 110 and the organic specimen 160 and for transferring that location data 194 to the processor means 130; a memory means 125 for storing anatomic model data 186 for at least part 155 of the organic specimen 160; the processor means 130 for identifying a region 220 of the organic specimen 160 associated with selected ultrasound data 187 using location data 194 and one or more sets of ultrasound data 187 resultant from reflections of recognized specimen features 210, creating an ultrasound image 180 from the selected ultrasound data 187, obtaining model extracted data 188 from the anatomic model data 186 corresponding to that of the selected ultrasound data 187 region 220, creating a model image 185 from the model extracted data 188, and transferring the ultrasound image 180 and the model image 185 to a display means 135; and the display means 135 configured for displaying the ultrasound image 180 and the model image 185.

In a fourth representative embodiment, a computer program product 133 stored on a non-transitory computer readable storage medium for carrying out a method 900 when executed on a computer 132 is disclosed. The method 900 comprises specifying a reference model image region 520a in model extracted data 188 obtained from anatomic model data 186 of at least part 155 of an organic specimen 160; instructing an ultrasound transducer 110 to transmit ultrasound incident waves 201 into the organic specimen 160 and receiving thereby ultrasound data 187 from ultrasound reflected waves 202 from specimen features 210 in the organic specimen 160, wherein positional awareness 194 of each ultrasound reflected wave 202 relative to the organic specimen 160 is maintained; identifying a reference propagation region 220a corresponding to the reference model image region 520a from paired recognized specimen features 210 in the ultrasound data 202 and in the model extracted data 188; instructing an ultrasound transducer 110 to transmit at least one subsequent ultrasound incident wave 201 into the organic specimen 160 and receiving thereby subsequent ultrasound data 187 from ultrasound reflected waves 202 from one or more specimen features 210, wherein positional awareness is maintained between the reference propagation region 220a and the propagation region 220 of the subsequent ultrasound data 187; and for the subsequent ultrasound data 187, creating an ultrasound image 180, creating a model image 185 for a model image region 520 from the anatomic model data 186 corresponding to the propagation region 220 of the subsequent ultrasound data 187, and instructing a display module 135 to display the ultrasound image 180 and the model image 185.

In an optional aspect of the fourth representative embodiment, the method 900 further comprising: identifying at least one specimen feature 210 on the ultrasound image 180 from a corresponding model feature 510 on the model image 185.

In an optional aspect of the fourth representative embodiment, wherein the reference model image region 520a is a plane 520a and is specified by three non-collinear model reference points 515a,515b,515c in the anatomic model data 186 of at least part 155 of the organic specimen 160.

In an optional aspect of the fourth representative embodiment, wherein the reference model image region 520a is a plane 520a and is specified by three non-collinear model reference points 515a,515b,515c in the anatomic model data 186 of at least part 155 of the organic specimen 160 and wherein the reference propagation region 220a in the organic specimen 160 is a plane 220a corresponding to the reference model image plane 520a and is identified when one or more ultrasound incident waves 201 are reflected separately or in combination from three specimen reference points 215a, 215b,215c corresponding to the three model reference points 515a,515b,515c.

In an optional aspect of the fourth representative embodiment, wherein the model extracted data 188 is stored in a memory module 125.

In an optional aspect of the fourth representative embodiment, wherein the ultrasound data 187 is stored in a memory module 125.

In an optional aspect of the fourth representative embodiment, wherein instructing the display module 135 to display the ultrasound image 180 and the model image 185 comprises: an instruction to display at least one static, two-dimensional ultrasound image 180 and its associated static, two-dimensional model image 185, and/or an instruction to display at least one static, three-dimensional ultrasound image 180 and its associated static, three-dimensional model image 185, and/or an instruction to display at least one set of time varying, two-dimensional ultrasound images 180 and its associated set of time varying, two-dimensional model images 185, and/or an instruction to display at least one set of time varying, three-dimensional ultrasound images 180 and its associated set of time varying, three-dimensional model images 185.

In an optional aspect of the fourth representative embodiment, wherein the anatomic model data 186 is stored in a memory module 125.

In an optional aspect of the fourth representative embodiment, wherein the display module 135 comprises a first display 140 and a second display 145 and wherein the ultrasound image 180 is displayed on the first display 140 and the model image 185 is displayed on the second display 145.

In an optional aspect of the fourth representative embodiment, wherein the ultrasound image 180 and the model image 185 are overlaid on the display module 135 or wherein the ultrasound image 180 and the model image 185 are displayed side-by-side on the display module 135.

In an optional aspect of the fourth representative embodiment, wherein the model image 185 and the ultrasound image 180 are scaled to each other.

In an optional aspect of the fourth representative embodiment, wherein the anatomic model data 186 is obtained from the Visible Human Project data 186 for a representative human male or a representative human female.

In an optional aspect of the fourth representative embodiment, wherein the anatomic model data 186 is for a representative human male or a representative human female.

In an optional aspect of the fourth representative embodiment, the method 900 further comprising: detecting a patient unique feature 450 in the organic specimen 160.

In a fifth representative embodiment, a non-transitory computer-readable medium 125 having computer-executable instructions for causing a computer 132 comprising a processor 130 and associated memory 125 to carry out a method 900 is disclosed. The method 900 comprises specifying a reference model image region 520a in model extracted data 188 obtained from anatomic model data 186 of at least part 155 of an organic specimen 160; instructing an ultrasound transducer 110 to transmit ultrasound incident waves 201 into the organic specimen 160 and receiving thereby ultrasound data 187 from ultrasound reflected waves 202 from specimen features 210 in the organic specimen 160, wherein positional awareness 194 of each ultrasound reflected wave 202 relative to the organic specimen 160 is maintained; identifying a reference propagation region 220a corresponding to the reference model image region 520a from paired recognized specimen features 210 in the ultrasound data 202 and in the model extracted data 188; instructing an ultrasound transducer 110 to transmit at least one subsequent ultrasound incident wave 201 into the organic specimen 160 and receiving thereby subsequent ultrasound data 187 from ultrasound reflected waves 202 from one or more specimen features 210, wherein positional awareness is maintained between the reference propagation region 220a and the propagation region 220 of the subsequent ultrasound data 187; and for the subsequent ultrasound data 187, creating an ultrasound image 180, creating a model image 185 for a model image region 520 from the anatomic model data 186 corresponding to the propagation region 220 of the subsequent ultrasound data 187, and instructing a display module 135 to display the ultrasound image 180 and the model image 185.

In representative embodiments, the anatomic model data 186 for at least part of the organic specimen 160 can be for a representative organic specimen, a representative human male, and/or a representative human female that is other than the organic specimen 160 or patient 160 from which ultrasound data 187 is obtained.

It will be appreciated that any module or component disclosed herein that executes instructions may include or otherwise have access to non-transient and tangible computer readable media such as storage media, computer storage media, or data storage devices (removable or non-removable) such as, for example, magnetic disks, optical disks, or tape data storage. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the server, any component of or related to the network, backend, etc., or accessible or connectable thereto. Any application or module herein described may be implemented using computer readable/executable instructions that may be stored or otherwise held by such computer readable media.

The representative embodiments, which have been described in detail herein, have been presented by way of example and not by way of limitation. It will be understood by those skilled in the art that various changes may be made in the form and details of the described embodiments resulting in equivalent embodiments that remain within the scope of the appended claims.

What is claimed is:

1. A method for using an ultrasound system comprising an ultrasound transducer and a location detection unit, the method comprising:
    transmitting one or more reference ultrasound incident waves into an organic specimen using the ultrasound transducer and receiving thereby reference ultrasound data from resultant ultrasound reflected waves from specimen features in the organic specimen,
        wherein positional awareness of each ultrasound reflected wave relative to the organic specimen is maintained using the location detection unit;
    identifying a reference propagation region in the organic specimen in which at least one of the one or more reference ultrasound incident waves was transmitted into the organic specimen and identifying a corresponding reference model image region in anatomic model data,
        wherein the anatomic model data correspond to at least part of the organic specimen; and
    transmitting at least one additional ultrasound incident wave into the organic specimen using the ultrasound transducer and receiving thereby additional ultrasound data from resultant ultrasound reflected waves from one or more specimen features,
        wherein positional awareness is maintained between the reference propagation region and a propagation region of the additional ultrasound data using the location detection unit.

2. The method as recited in claim 1, wherein the reference model image region in the anatomic model data and the corresponding reference propagation region in the organic specimen are identified using model features in the anatomic model data and corresponding specimen features in the reference ultrasound data.

3. The method as recited in claim 1, further comprising:
    creating an ultrasound image using selected ultrasound data.

4. The method as recited in claim 1, further comprising:
    creating a model image for a model image region corresponding to the propagation region of selected ultrasound data using the anatomic model data.

5. The method as recited in claim 1, further comprising:
    identifying a model feature in the anatomic model data that corresponds to a selected specimen feature in the ultrasound data and/or
    identifying another specimen feature in the ultrasound data that corresponds to another model feature in the anatomic model data.

6. The method as recited in claim 1, wherein the anatomic model data are obtained from at least part of data for a representative human male or a representative human female, and/or from at least part of a representative organic specimen that is other than the organic specimen from which the ultrasound data are obtained, and/or from at least portions of photographs and/or visual images of physical cross-sections of another representative organic specimen.

7. The method as recited in claim 1, further comprising:
    selecting a model image region in the anatomic model data and selecting a corresponding propagation region in the organic specimen;
    creating a model image using anatomic model data from the selected model image region;
    creating an ultrasound image using ultrasound data from the selected propagation region; and
    displaying the model image and the ultrasound image on a display module.

8. The method as recited in claim 7, further comprising:
    identifying a model feature in the model image that corresponds to a selected specimen feature in the ultrasound image and/or
    identifying another specimen feature in the ultrasound image that corresponds to another model feature in the model image.

9. The method as recited in claim 7, wherein the ultrasound image and the model image displayed on the display module comprise:
at least one static, two-dimensional ultrasound image and associated at least one static, two-dimensional model image, and/or
at least one static, three-dimensional ultrasound image and associated at least one static, three-dimensional model image, and/or
at least one set of time varying, two-dimensional ultrasound images and associated at least one set of time varying, two-dimensional model images, and/or
at least one set of time varying, three-dimensional ultrasound images and associated at least one set of time varying, three-dimensional model images.

10. The method as recited in claim 7, wherein the display module comprises a first display and a second display and wherein the ultrasound image is displayed on the first display and the model image is displayed on the second display.

11. The method as recited in claim 7, wherein the ultrasound image and the model image are overlaid on the display module or wherein the ultrasound image and the model image are displayed side-by-side on the display module.

12. The method as recited in claim 1, further comprising: detecting a unique specimen feature in, and/or an aberrant feature in, and/or an instrument inserted into the organic specimen.

13. A system, comprising:
a processor and a non-volatile memory, the processor configured
to issue an instruction to transmit one or more reference ultrasound incident waves into an organic specimen and to receive thereby reference ultrasound data from resultant ultrasound reflected waves from specimen features in the organic specimen,
wherein positional awareness of each ultrasound reflected wave relative to the organic specimen is maintained;
to identify a reference propagation region in the organic specimen in which at least one of the one or more reference ultrasound incident waves was transmitted into the organic specimen and a corresponding reference model image region in anatomic model data, wherein the anatomic model data correspond to at least part of the organic specimen; and
to issue an instruction to transmit at least one additional ultrasound incident wave into the organic specimen and to receive thereby additional ultrasound data from resultant ultrasound reflected waves from one or more specimen features,
wherein positional awareness is maintained between the reference propagation region and a propagation region of the additional ultrasound data.

14. The system as recited in claim 13, wherein the processor is further configured to identify the reference model image region in the anatomic model data and the corresponding reference propagation region in the organic specimen using model features in the anatomic model data and corresponding specimen features in the reference ultrasound data.

15. The system as recited in claim 13, wherein the processor is further configured to create an ultrasound image using selected ultrasound data.

16. The system as recited in claim 13, wherein the processor is further configured to create a model image for a model image region corresponding to the propagation region of selected ultrasound data using the anatomic model data.

17. The system as recited in claim 13, wherein the processor is further configured to identify a model feature in the anatomic model data that corresponds to a selected specimen feature in the ultrasound data and/or to identify another specimen feature in the ultrasound data that corresponds to another model feature in the anatomic model data.

18. The system as recited in claim 13, wherein the anatomic model data are obtained from at least part of data for a representative human male or a representative human female, and/or from at least part of a representative organic specimen that is other than the organic specimen from which the ultrasound data are obtained, and/or from at least portions of photographs and/or visual images of physical cross-sections of another representative organic specimen.

19. The system as recited in claim 13, further comprising:
a display module configured to display an ultrasound image and a model image,
wherein, following selection of a model image region in the anatomic model data and a corresponding propagation region in the organic specimen, the processor is further configured to create the model image using anatomic model data from the selected model image region and to create the ultrasound image using ultrasound data from the selected propagation region.

20. The system as recited in claim 19, wherein the processor is further configured to identify a model feature in the model image that corresponds to a selected specimen feature in the ultrasound image and/or to identify another specimen feature in the ultrasound image that corresponds to another model feature in the model image.

21. The system as recited in claim 19, wherein the ultrasound image and the model image displayed on the display module comprise:
at least one static, two-dimensional ultrasound image and associated at least one static, two-dimensional model image, and/or
at least one static, three-dimensional ultrasound image and associated at least one static, three-dimensional model image, and/or
at least one set of time varying, two-dimensional ultrasound images and associated at least one set of time varying, two-dimensional model images, and/or
at least one set of time varying, three-dimensional ultrasound images and associated at least one set of time varying, three-dimensional model images.

22. The system as recited in claim 19, wherein the display module comprises a first display and a second display and wherein the first display is configured to display the ultrasound image and the second display is configured to display the model image.

23. The system as recited in claim 19, wherein the ultrasound image and the model image are overlaid on the display module or wherein the ultrasound image and the model image are displayed side-by-side on the display module.

24. The system as recited in claim 13, wherein the processor is further configured to detect a unique specimen feature in, and/or an aberrant feature in, and/or an instrument inserted into the organic specimen.

25. The system as recited in claim 13, further comprising:
a location detection unit configured to detect at least one location for reception of at least one ultrasound reflected wave from specimen features of the organic specimen relative to a selected reception location and to transfer that relative location data to the processor.

26. A non-transitory computer-readable medium having computer-executable instructions for causing a computer comprising a processor and associated memory to carry out a method, the method comprising:

issuing an instruction to transmit one or more reference ultrasound incident waves into an organic specimen and receiving thereby reference ultrasound data from resultant ultrasound reflected waves from specimen features in the organic specimen, wherein positional awareness of each ultrasound reflected wave relative to the organic specimen is maintained;

identifying a reference propagation region in the organic specimen in which at least one of the one or more reference ultrasound incident waves was transmitted into the organic specimen and identifying a corresponding reference model image region in anatomic model data, wherein the anatomic model data correspond to at least part of the organic specimen; and issuing an instruction to transmit at least one additional ultrasound incident wave into the organic specimen and receiving thereby additional ultrasound data from resultant ultrasound reflected waves from one or more specimen features, wherein positional awareness is maintained between the reference propagation region and a propagation region of the additional ultrasound data.

27. The non-transitory computer-readable medium as recited in claim 26, wherein the reference model image region in the anatomic model data and the corresponding reference propagation region in the organic specimen are identified using model features in the anatomic model data and corresponding specimen features in the reference ultrasound data.

28. The non-transitory computer-readable medium as recited in claim 26, the method further comprising:

creating an ultrasound image using selected ultrasound data.

29. The non-transitory computer-readable medium as recited in claim 26, the method further comprising:

creating a model image for a model image region corresponding to the propagation region of selected ultrasound data using the anatomic model data.

30. The non-transitory computer-readable medium as recited in claim 26, the method further comprising:

identifying a model feature in the anatomic model data that corresponds to a selected specimen feature in the ultrasound data and/or identifying another specimen feature in the ultrasound data that corresponds to another model feature in the anatomic model data.

31. The non-transitory computer-readable medium as recited in claim 26, wherein the anatomic model data are obtained from at least part of data for a representative human male or a representative human female, and/or from at least part of a representative organic specimen that is other than the organic specimen from which the ultrasound data are obtained, and/or from at least portions of photographs and/or visual images of physical cross-sections of another representative organic specimen.

32. The non-transitory computer-readable medium as recited in claim 26, the method further comprising:

selecting a model image region in the anatomic model data and selecting a corresponding propagation region in the organic specimen;

creating a model image using anatomic model data from the selected model image region;

creating an ultrasound image using ultrasound data from the selected propagation region; and instructing a display module to display the model image and the ultrasound image.

33. The non-transitory computer-readable medium as recited in claim 32, the method further comprising:

identifying a model feature in the model image that corresponds to a selected specimen feature in the ultrasound image and/or identifying another specimen feature in the ultrasound image that corresponds to another model feature in the model image.

34. The non-transitory computer-readable medium as recited in claim 32, wherein the ultrasound image and the model image displayed on the display module comprise:

at least one static, two-dimensional ultrasound image and associated at least one static, two-dimensional model image, and/or at least one static, three-dimensional ultrasound image and associated at least one static, three-dimensional model image, and/or at least one set of time varying, two-dimensional ultrasound images and associated at least one set of time varying, two-dimensional model images, and/or at least one set of time varying, three-dimensional ultrasound images and associated at least one set of time varying, three-dimensional model images.

35. The non-transitory computer-readable medium as recited in claim 32, wherein the display module comprises a first display and a second display and wherein the ultrasound image is displayed on the first display and the model image is displayed on the second display.

36. The non-transitory computer-readable medium as recited in claim 32, wherein the ultrasound image and the model image are overlaid on the display module or wherein the ultrasound image and the model image are displayed side-by-side on the display module.

37. The non-transitory computer-readable medium as recited in claim 26, the method further comprising:

detecting a unique specimen feature in, and/or an aberrant feature in, and/or an instrument inserted into the organic specimen.

* * * * *